(12) United States Patent
Hashimoto et al.

(10) Patent No.: US 8,058,037 B2
(45) Date of Patent: Nov. 15, 2011

(54) PROTEIN AND DNA ENCODING THE PROTEIN

(75) Inventors: Shin-ichi Hashimoto, Yamaguchi (JP);
Yoshiyuki Yonetani, Tokyo (JP);
Masaki Maeda, Tokyo (JP)

(73) Assignee: Kyowa Hakko Bio Co., Ltd., Tokyo (JP)

( * ) Notice: Subject to any disclaimer, the term of this patent is extended or adjusted under 35 U.S.C. 154(b) by 190 days.

(21) Appl. No.: 12/095,244

(22) PCT Filed: Nov. 29, 2006

(86) PCT No.: PCT/JP2006/323757
§ 371 (c)(1),
(2), (4) Date: Aug. 26, 2008

(87) PCT Pub. No.: WO2007/063866
PCT Pub. Date: Jun. 7, 2007

(65) Prior Publication Data
US 2010/0062486 A1    Mar. 11, 2010

(30) Foreign Application Priority Data
Nov. 29, 2005    (JP) ................ 2005-344312

(51) Int. Cl.
*C12P 7/00* (2006.01)
*C12P 7/02* (2006.01)

(52) U.S. Cl. ........................... 435/132; 435/155
(58) Field of Classification Search .................. None
See application file for complete search history.

(56) References Cited

U.S. PATENT DOCUMENTS

| | | | |
|---|---|---|---|
| 4,346,227 | A | 8/1982 | Terahara et al. |
| 4,410,629 | A | 10/1983 | Terahara et al. |
| 4,448,979 | A | 5/1984 | Terahara et al. |
| 4,686,191 | A | 8/1987 | Itoh et al. |
| 5,160,735 | A | 11/1992 | Yasumura et al. |
| 5,218,092 | A | 6/1993 | Sasaki et al. |
| 5,342,775 | A | 8/1994 | Yasumura et al. |
| 6,043,064 | A | 3/2000 | Davis et al. |
| 6,245,535 | B1 | 6/2001 | Takano et al. |
| 6,468,780 | B2 | 10/2002 | Takano et al. |
| 6,893,848 | B1 | 5/2005 | Yokoi et al. |
| 6,946,270 | B1 | 9/2005 | Hashimoto et al. |
| 7,049,111 | B1 | 5/2006 | Endo et al. |
| 7,186,532 | B2 | 3/2007 | Ikeda et al. |
| 7,470,528 | B2 | 12/2008 | Endo et al. |
| 2006/0154348 | A1 | 7/2006 | Endo et al. |
| 2006/0234337 | A1 | 10/2006 | Arisawa et al. |
| 2008/0261273 | A1 | 10/2008 | Endo et al. |

FOREIGN PATENT DOCUMENTS

| | | |
|---|---|---|
| EP | 0 243 153 | 10/1987 |
| EP | 0 263 716 | 4/1988 |
| EP | 1 148 122 | 10/2001 |
| JP | 57-50894 | 3/1982 |
| JP | 58-110600 | 7/1983 |
| JP | 63-299 | 1/1988 |
| JP | 63-233798 | 9/1988 |
| JP | 63-248394 | 10/1988 |
| JP | 2-227075 | 9/1990 |
| JP | 2-257891 | 10/1990 |
| JP | 3-22979 | 1/1991 |
| JP | 7-184670 | 7/1995 |
| WO | 96/40863 | 12/1996 |
| WO | 99/07872 | 2/1999 |
| WO | 00/43533 | 7/2000 |
| WO | 00/44886 | 8/2000 |
| WO | 00/63388 | 10/2000 |
| WO | 02/099109 | 12/2002 |
| WO | 03/087381 | 10/2003 |

OTHER PUBLICATIONS

Kunst et al., "The complete genome sequence of the Gram-positive bacterium *Bacillus subtilis*" Nature, vol. 390, pp. 249-256 (1997).
Hashimoto et al., "Search for a bacteria having compactin hydroxylating activity," *Japan Society for Bioscience, Biotechnology, and Agrochemistry* 2A11a11 (2004), along with an English language abstract thereof.
Yonetani et al., "Cloning a gene encoding compactin hydroxylating enzyme," *Japan Society for Bioscience, Biotechnology, and Agrochemistry* 2A11a12 (2004), along with an English language abstract thereof.
Endo et al., ML-236A, ML-236B, and ML-236C, New Inhibitors of Cholesterogenesis Produced by *Penicillium citrinum*, *The Journal of Antibiotics*, vol. 29, pp. 1346-1348 (1976).
English language Abstract of JP 57-50894.
English language Abstract of JP 7-184670.
Okayama et al., "A cDNA Cloning Vector That Permits Expression of cDNA Inserts in Mammalian Cells" *Mol. Cell. Biol.*, vol. 3, No. 2, pp. 280-289 (1983).
Gerhus et al., "*Paracoccus denitrificans* Cytochrome $c_1$ Gene Replacement Mutants" *J. Bacteriol.*, vol. 172, No. 5, pp. 2392-2400 (1990).
English Language abstract of JP 58-110600.
Sekine et al., "Cloning and expression of cDNA for salmon growth hormone in *Escherichia coli*" *Proc. Natl. Acad. Sci. USA*, vol. 82, pp. 4306-4310 (1985).
English Language abstract of JP 63-233798.
Cohen et al., "Nonchromosomal Antibiotic Resistance in Bacteria: Genetic Transformation of *Escherichia coli* by R-Factor DNA" *Proc. Nat. Acad. Sci. USA*, vol. 69, No. 8, pp. 2110-2114 (1972).
English Language abstract of JP 63-248394.
Hinnen et al., "Transformation of yeast" *Proc. Natl. Acad. Sci. USA*, vol. 75, No. 4, pp. 1929-1933 (1978).

(Continued)

*Primary Examiner* — Nashaat Nashed
(74) *Attorney, Agent, or Firm* — Greenblum & Bernstein, PLC

(57) ABSTRACT

The present invention provides a protein comprising the amino acid sequence as shown in any one of SEQ ID NOS: 1 to 3 (except for proteins of the amino acid sequences as shown in SEQ ID NOS: 4 to 6), and a process for industrially advantageously producing a compound that inhibits HMG-CoA reductase and has an action to decrease serum cholesterol, using DNA encoding the protein comprising the amino acid sequence as shown in any one of SEQ ID NOS: 1 to 3 (except for DNA encoding the protein comprising the amino acid sequence as shown in SEQ ID NO: 4).

2 Claims, 1 Drawing Sheet

OTHER PUBLICATIONS

Ito et al., "Transformation of Intact Yeast Cells Treated with Alkali Cations" *J. Bacteriol.*, vol. 153, No. 1, pp. 163-168 (1983).

English Language abstract of JP 3-22979.

English Language abstract of JP 2-227075.

Feigner et al., "Lipofection: A highly efficient, lipid-mediated DNA-transfection procedure" *Proc. Natl. Acad. Sci. USA*, vol. 84, pp. 7413-7417 (1987).

English Language abstract of JP 2-257891.

Koizumi et al., "Production of riboflavin by metabolically engineered *Corynebacterium ammoniagenes*" *Appl. Microbiol. Biotechnol.*, vol. 53, pp. 674-679 (2000).

U.S. Appl. No. 12/272,448 to Endo et al., entitled "Process for Producing HMG-CoA Reductase Inhibitor," filed on Nov. 17, 2008.

Database UniProt May 30, 2000 (May 3, 2000). Rivolta, C. et al.: "A 35.7 kb DNA fragment from *B. subtilis* chromosome containing a putative 12.3 kb operon involved in hexuronate catabolism and a perfect catabolite-responsive element" XP002515180 retrieved from IBIS Database accession No. YJIB_BACSU O34374.

[Figure 1]
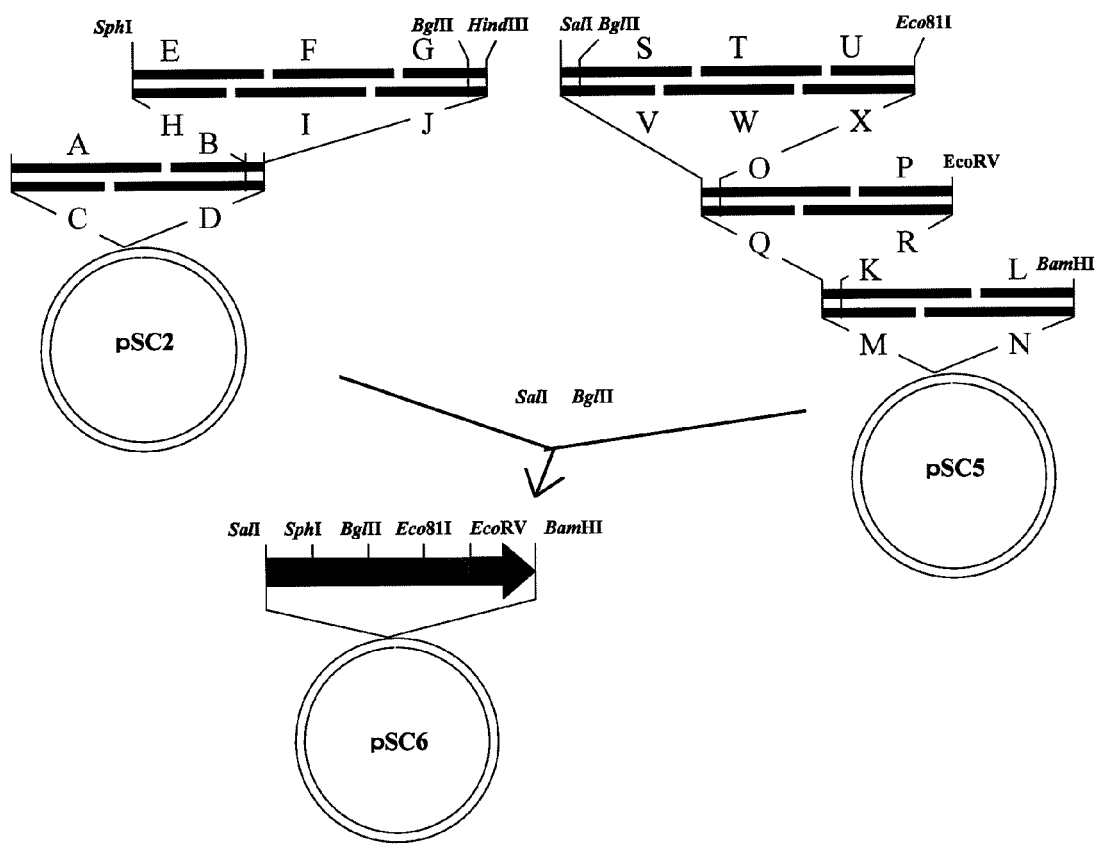
[Figure 2]
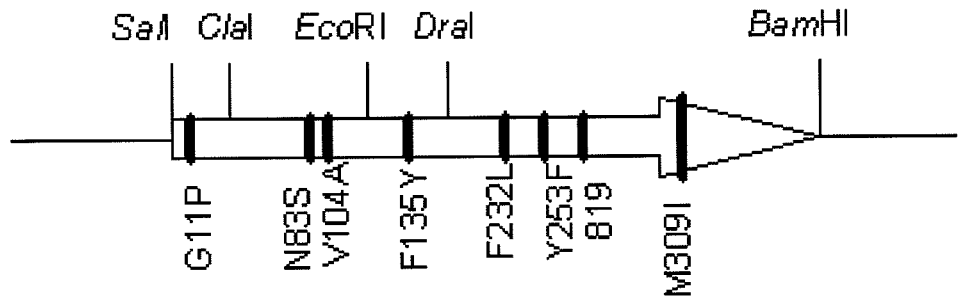

PROTEIN AND DNA ENCODING THE PROTEIN

SEQUENCE LISTING

The instant application contains a Sequence Listing which has been submitted in ASCII format via EFS-Web and is hereby incorporated by reference in its entirety. Said ASCII copy, created on May 12, 2011, is named P34550.txt and is 58,280 bytes in size.

TECHNICAL FIELD

The present invention relates to a protein having an activity of producing a compound that inhibits hydroxymethylglutaryl-CoA (HMG-CoA) reductase and has an action to decrease serum cholesterol, DNA encoding the protein, a transformant having the DNA, and a process for producing the aforementioned compound using the protein or the transformant.

BACKGROUND ART

It has been known that, among compounds represented by Formula (XI) [hereinafter referred to as compound (VI-a)]:

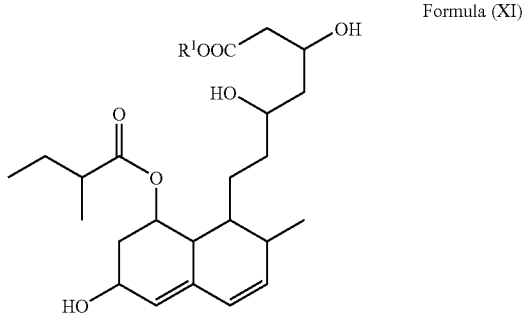

Formula (XI)

(wherein $R^1$ represents a hydrogen atom, substituted or unsubstituted alkyl, or alkali metal), a compound wherein, in the above Formula (XI), $R^1$ represents a hydrogen atom or alkali metal, or a closed lactone form of the compound (VI-a) represented by Formula (XII) [hereinafter referred to as compound (VI-b)]:

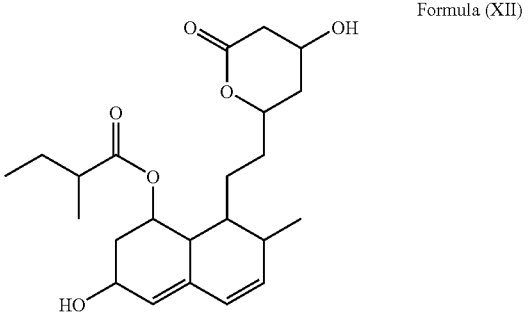

Formula (XII)

inhibits HMG-CoA reductase and has an action to decrease serum cholesterol or the like (Non-Patent Document 1).

Several reports have been published regarding a method using microorganisms to form the compound (VI-a) or the compound (VI-b) from a compound represented by Formula (IX) [hereinafter referred to as compound (V-a)]:

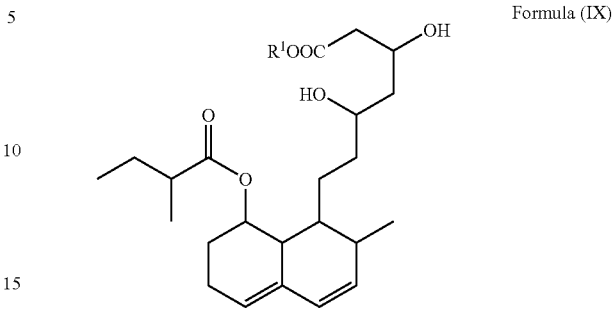

Formula (IX)

(wherein $R^1$ represents a hydrogen atom, substituted or unsubstituted alkyl, or alkali metal), or a closed lactone form of the compound (V-a) represented by Formula (X) [hereinafter referred to as compound (V-b)]:

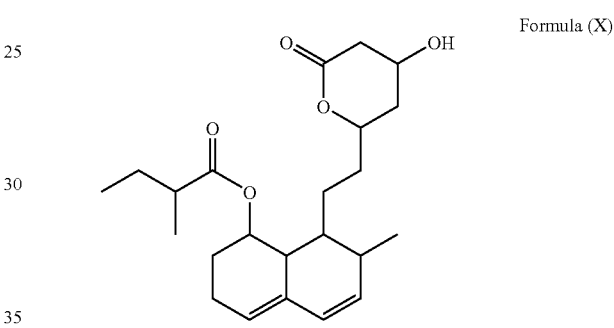

Formula (X)

That is to say, Patent Document 1 describes a method using filamentous fungi, and Patent Documents 2 and 3 describe a method using actinomycetes. However, since such microorganisms extend hypha for their growth, if they are allowed to grow in a fermenter, the viscosity of the culture solution increases. Thus, it leads to lack of oxygen, and the culture solution becomes inhomogeneous, resulting in a decrease in the reaction efficiency. In order to solve the problem regarding such lack of oxygen so as to maintain the culture solution homogeneous, the stirring speed in the fermenter should be increased. However, if the stirring speed is increased, hypha is sheared, and the activity of microorganisms is likely to decrease (Non-Patent Document 2).

As methods for solving such problems, Patent Document 4 describes a method using *Bacillus subtilis*, and Patent Document 5 describes a method using microorganisms that do not form spores and do not form hypha. However, the two above methods are problematic in that they require a long period of time for culture and/or reaction, and in that the yield of the compound (VI-a) or (VI-b) of interest to the raw material compound (V-a) or (V-b) is low. Accordingly, it is hard to say that these production methods are industrially advantageous.

As a method for solving the aforementioned problems, there is a method of amplifying an enzyme gene that catalyzes a reaction of forming the compound (VI-a) or (VI-b) from the compound (V-a) or (V-b), so as to improve a reaction rate or a yield. The enzyme gene catalyzing the aforementioned reaction has already been obtained from *Bacillus subtilis* by the present inventors (Patent Document 6). The effect of increasing the activity of forming the aforementioned compound was obtained by introduction of the gene. However, in terms of a production rate or a yield, industrially satisfactory results were not obtained.

[Non-Patent Document 1] The Journal of Antibiotics 29, 1346 (1976)
[Non-Patent Document 2] *Hakko Kogaku no Kiso* (Basic Fermentation Technology), pp. 169-190, P. F. Stansbury, A. Whitaker, Japan Scientific Societies Press (1988)
[Patent Document 1] Japanese Published Unexamined Patent Application No. 50894/1982
[Patent Document 2] Japanese Published Unexamined Patent Application No. 184670/1995
[Patent Document 3] International Publication WO96/40863 pamphlet
[Patent Document 4] International Publication WO99/07872 pamphlet
[Patent Document 5] International Publication WO00/43533 pamphlet
[Patent Document 6] International Publication WO00/44886 pamphlet

DISCLOSURE OF THE INVENTION

Problems to be Solved by the Invention

It is an object of the invention of the present application to provide a protein having an activity of forming a compound that inhibits HMG-CoA reductase and has an action to decrease serum cholesterol, DNA encoding the protein, a transformant having the DNA, and an industrially advantageous process for producing the aforementioned compound using the aforementioned protein or the aforementioned transformant.

Means for Solving the Problem

The present invention relates to the following (1) to (22).
(1) A protein comprising the amino acid sequence as shown in any one of SEQ ID NOS: 1 to 3, provided that proteins of the amino acid sequences as shown in SEQ ID NOS: 4 to 6 are excluded.
(2) A DNA encoding a protein comprising the amino acid sequence as shown in any one of SEQ ID NOS: 1 to 3, provided that DNA encoding the protein of the amino acid sequence as shown in SEQ ID NO: 4 is excluded.
(3) A DNA comprising the nucleotide sequence as shown in SEQ ID NO: 7.
(4) A recombinant DNA comprising the DNA according to (2) or (3) above.
(5) A transformant obtained by introducing the recombinant DNA according to (4) above into host cells.
(6) The transformant according to (5) above, wherein the host cells are microorganisms belonging to the genus *Escherichia, Bacillus, Corynebacterium, Streptomyces, Aspergillus*, or *Penicillium*.
(7) The transformant according to (5) above, wherein host cells are microorganisms belonging to *Escherichia coli, Bacillus subtilis, Bacillus megaterium, Corynebacterium glutamicum, Corynebacterium ammoniagenes, Streptomyces lividans, Aspergillus terreus*, or *Penicillium citrinum*.

(8) A process for producing a compound represented by Formula (III):

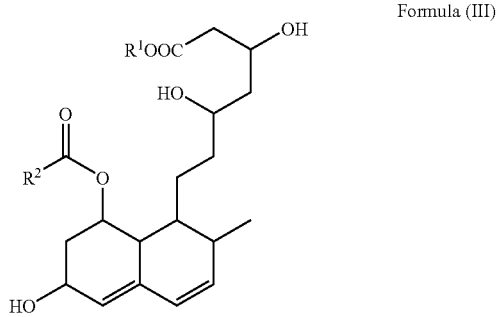

Formula (III)

(wherein $R^1$ represents a hydrogen atom, substituted or unsubstituted alkyl, or alkali metal, and $R^2$ represents substituted or unsubstituted alkyl or aryl) [hereinafter referred to as compound (II-a)] or a closed lactone form of the compound (II-a) represented by Formula (IV):

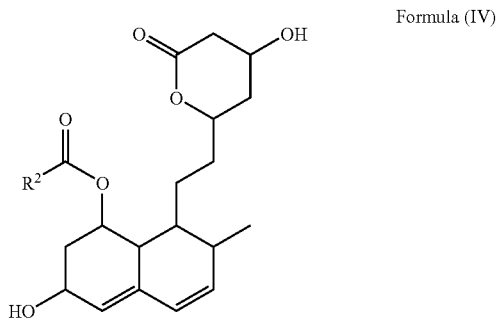

Formula (IV)

(wherein $R^2$ represents substituted or unsubstituted alkyl or aryl) [hereinafter referred to as compound (II-b)], which comprises allowing the protein according to (1) or (2) to come into contact with a compound represented by Formula (I) [hereinafter referred to as compound (I-a)]:

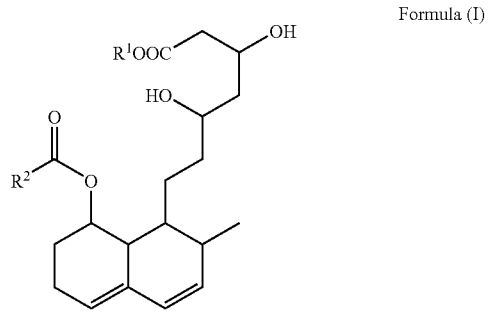

Formula (I)

(wherein $R^1$ represents a hydrogen atom, substituted or unsubstituted alkyl, or alkali metal, and $R^2$ represents substituted or unsubstituted alkyl or aryl), or a closed lactone form of the compound (I-a) represented by Formula (II) [hereinafter referred to as compound (I-b)]:

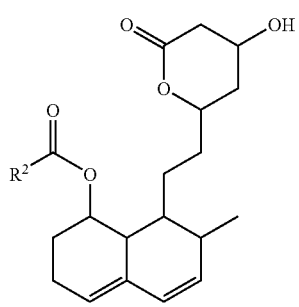

Formula (II)

(wherein R² represents substituted or unsubstituted alkyl or aryl), so as to form compound (II-a) or compound (II-b) and recovering the compound (II-a) or the compound (II-b).

(9) A process for producing compound (II-a) or compound (II-b), which comprises allowing a culture of the transformant according to any one of (5) to (7) above or a treated product of the culture to come into contact with compound (I-a) or compound (I-b) in an aqueous medium, forming and accumulating compound (II-a) or compound (II-b) in the aqueous medium, and recovering the compound (II-a) or the compound (II-b) from the aqueous medium.

(10) The production process according to (8) or (9) above, wherein the compound (I-a) is a compound represented by Formula (V) [hereinafter referred to as compound (III-a)]:

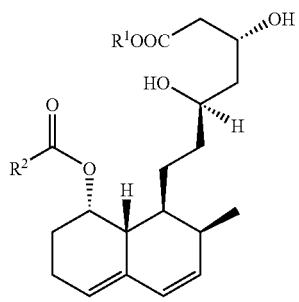

Formula (V)

(wherein R¹ represents a hydrogen atom, substituted or unsubstituted alkyl, or alkali metal, and R² represents substituted or unsubstituted alkyl or aryl), the compound (I-b) is a compound represented by Formula (VI) [hereinafter referred to as compound (III-b)]:

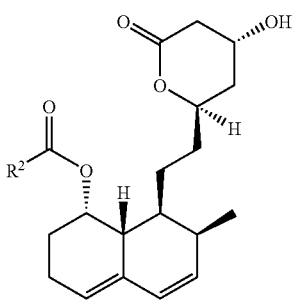

Formula (VI)

(wherein R² represents substituted or unsubstituted alkyl or aryl), the compound (II-a) is a compound represented by Formula (VII) [hereinafter referred to as compound (IV-a)]:

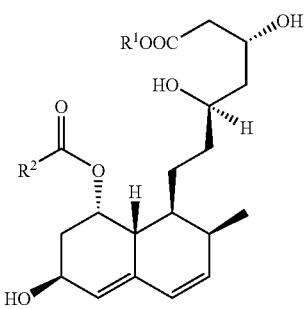

Formula (VII)

(wherein R¹ represents a hydrogen atom, substituted or unsubstituted alkyl, or alkali metal, and R² represents substituted or unsubstituted alkyl or aryl), and the compound (II-b) is a compound represented by Formula (VIII) [hereinafter referred to as compound (IV-b)]:

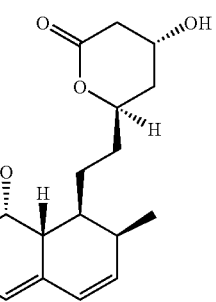

Formula (VIII)

(wherein R² represents substituted or unsubstituted alkyl or aryl).

(11) The production process according to (8) or (9) above, wherein the compound (I-a) is a compound represented by Formula (IX) [hereinafter referred to as compound (V-a)]:

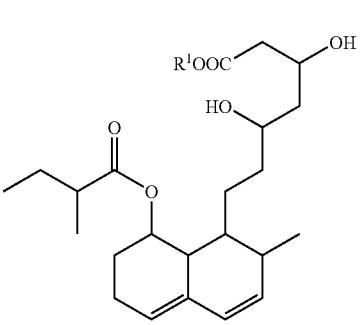

Formula (IX)

(wherein R¹ represents a hydrogen atom, substituted or unsubstituted alkyl, or alkali metal), the compound (I-b) is a compound represented by Formula (X) [hereinafter referred to as compound (V-b)]:

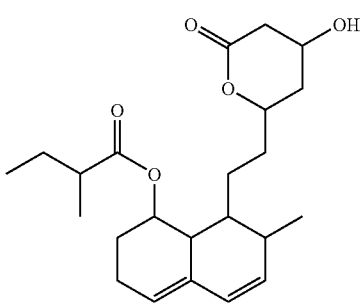

Formula (X)

the compound (II-a) is a compound represented by Formula (XI) [hereinafter referred to as compound (VI-a)]:

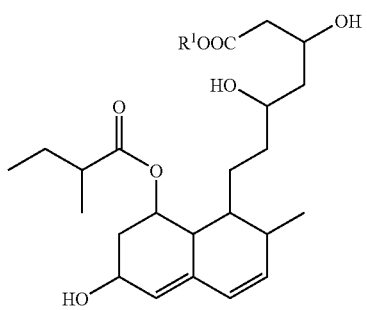

Formula (XI)

(wherein $R^1$ represents a hydrogen atom, substituted or unsubstituted alkyl, or alkali metal), and the compound (II-b) is a compound represented by Formula (XII) [hereinafter referred to as compound (VI-b)]:

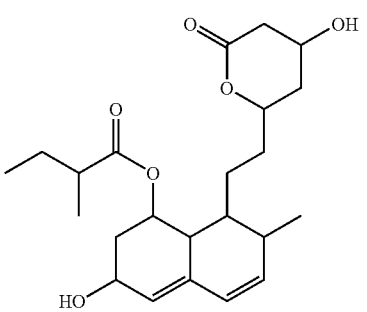

Formula (XII)

(12) The production process according to (8) or (9) above, wherein the compound (I-a) is a compound represented by Formula (XIII) [hereinafter referred to as compound (VII-a)]:

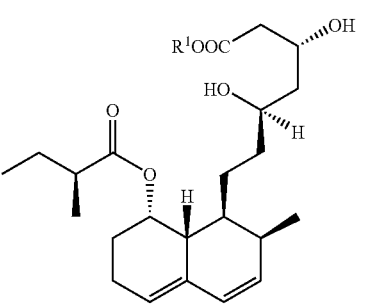

Formula (XIII)

(wherein $R^1$ represents a hydrogen atom, substituted or unsubstituted alkyl, or alkali metal), the compound (I-b) is a compound represented by Formula (XIV) [hereinafter referred to as compound (VII-b)]:

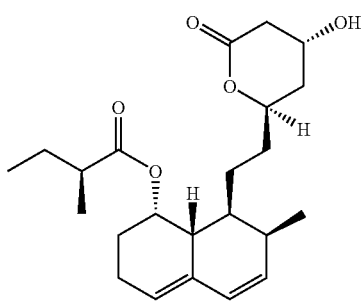

Formula (XIV)

the compound (II-a) is a compound represented by Formula (XV) [hereinafter referred to as compound (VIII-a)]:

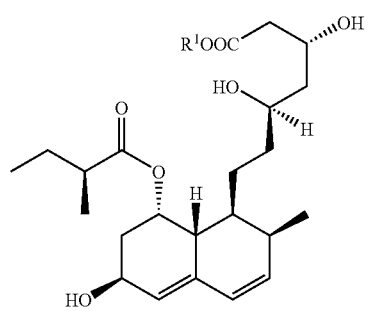

Formula (XV)

(wherein $R^1$ represents a hydrogen atom, substituted or unsubstituted alkyl, or alkali metal), and the compound (II-b) is a compound represented by Formula (XVI) [hereinafter referred to as compound (VIII-b)]:

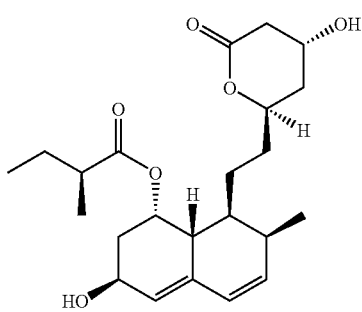

Formula (XVI)

(13) The production process according to (8) or (9) above, wherein the compound (II-b) is obtained by forming a lactone from the compound (II-a).
(14) The production process according to (8) or (9) above, wherein the compound (II-a) is obtained by the ring-opening of the lactone of the compound (II-b).
(15) The production process according to (10) above, wherein the compound (III-b) is obtained by forming a lactone from the compound (III-a).
(16) The production process according to (10) above, wherein the compound (IV-a) is obtained by the ring-opening of the lactone of the compound (IV-b).

(17) The production process according to (11) above, wherein the compound (V-b) is obtained by forming of a lactone from the compound (V-a).
(18) The production process according to (11) above, wherein the compound (VI-a) is obtained by the ring-opening of the lactone of the compound (VI-b).
(19) The production process according to (12) above, wherein the compound (VII-b) is obtained by forming a lactone from the compound (VII-a).
(20) The production process according to (12) above, wherein the compound (VIII-a) is obtained by the ring-opening of the lactone of the compound (VIII-b).
(21) The production process according to any one of (9) to (12) above, wherein the treated culture of the transformant is a treated culture selected from a concentrated culture, a dried culture, a freeze-dried culture, cells obtained from the culture, dried cells, freeze-dried cells, surfactant-treated cells, enzyme-treated cells, ultrasonic-treated cells, mechanically crushed cells, solvent-treated cells, protein fraction of the cells, and immobilized cells or treated cells.
(22) A process for producing a protein according to (1) above, which comprises culturing the transformant according to any one of (5) to (7) above in a medium, forming and accumulating the protein according to (1) above in the culture, and recovering the protein from the culture.

Effects of the Invention

According to the present invention, a compound that inhibits HMG-CoA reductase and has an action to decrease serum cholesterol can be efficiently and industrially produced.

BRIEF DESCRIPTION OF THE DRAWINGS

FIG. 1 is a view showing a production process of pSC6.
FIG. 2 is a view showing mutated sites in an yjiB gene on pSYN2-39 and the restriction sites. The arrow indicates an yjiB gene region, and the heavy lines indicate mutation positions.

BEST MODE FOR CARRYING OUT THE INVENTION

The invention of the present application will be described in detail below.
1. Protein of the Present Invention
The protein of the present invention is a protein comprising the amino acid sequence as shown in any one of SEQ ID NOS: 1 to 3, except for proteins of the amino acid sequences as shown in SEQ ID NOS: 4 to 6.

In addition, the protein of the present invention also includes a protein, which comprises an amino acid sequence having a substitution, deletion, or addition of 1 to 50, preferably 1 to 20, more preferably 1 to 15, further more preferably 1 to 10, particularly preferably 1 to 5, and the most preferably 1 to 3 amino acid residues, other than amino acids represented by Xaa, with respect to the amino acid sequence as shown in any one of SEQ ID NOS: 1 to 3, and which has an activity of converting the compound represented by the aforementioned Formula (I) (wherein $R^1$ represents a hydrogen atom, substituted or unsubstituted alkyl, or alkali metal, and $R^2$ represents substituted or unsubstituted alkyl or aryl) [hereinafter referred to as compound (I-a)], or the closed lactone form of the compound (I-a) represented by the aforementioned Formula (II) (wherein $R^2$ represents substituted or unsubstituted alkyl or aryl) [hereinafter referred to as compound (I-b)] to a compound represented by Formula (III) (wherein $R^1$ represents a hydrogen atom, substituted or unsubstituted alkyl, or alkali metal, and $R^2$ represents substituted or unsubstituted alkyl or aryl) [hereinafter referred to as compound (II-a)], or a closed lactone form of the compound (II-a) represented by Formula (IV) (wherein $R^2$ represents substituted or unsubstituted alkyl or aryl) [hereinafter referred to as compound (II-b)].

2. DNA of the Present Invention
Examples of the DNA of the present invention include DNAs encoding the proteins comprising the amino acid sequences as shown in SEQ ID NOS: 1 to 3 and DNA comprising the nucleotide sequence as shown in SEQ ID NO: 7, except for DNA encoding the protein of the amino acid sequence as shown in SEQ ID NO: 4.

DNAs of the nucleotide sequences as shown in SEQ ID NOS: 8 and 9 may be excluded from the DNA of the present invention.

3. Method for Producing DNA of the Present Invention
By synthesizing DNA encoding the protein comprising the amino acid sequence as shown in any one of SEQ ID NOS: 1 to 3 according to a known chemical synthesis method, the DNA of the invention of the present application can be produced. The synthesis of DNA can be carried out using a commercially available DNA synthesizer (for example, ABI-381A manufactured by PE BioSystems, etc.). Instead of synthesizing full-length DNA at a time, the DNA of the present invention can also be produced by synthesizing several DNA fragments and then successively ligating each fragments.

Moreover, the DNA of the present invention can also be produced by synthesizing DNA of the nucleotide sequence as shown in SEQ ID NO: 9 and then introducing a mutation into the DNA according to a known method. Otherwise, the DNA of the present invention can also be produced by combining the thus obtained mutated sites using restriction enzymes or the like.

Specifically, the DNA of the present invention can be produced by the method as described below. It is to be noted that operations on DNA, transformation of *Escherichia coli*, the recovery of a plasmid from *Escherichia coli*, etc. can be carried out according to conventional methods, for example, the methods described in Molecular cloning, A laboratory manual, Third Edition, Cold Harbor Laboratory Press (2001) (hereinafter abbreviated as Molecular Cloning $3^{rd}$ edition), Current Protocols in Molecular Biology, Supplements 1 to 38, John Wiley & Sons (1987-1997), DNA Cloning 1: Core Techniques, A Practical Approach, Second Edition, Oxford University Press (1995), etc., or by using commercially available kits.

First, a partial sequence obtained by division of the nucleotide sequence as shown in SEQ ID NO: 9 is synthesized. Preferably, in order to facilitate the subsequent ligation operation, a nucleotide sequence complementary to the aforementioned partial sequence is introduced as a protruding site, or a restriction site is added, as appropriate. Examples of the aforementioned partial sequence include DNAs having the nucleotide sequences as shown in SEQ ID NOS: 10 to 33. As shown in FIG. 1, the partial sequence can be divided into five blocks having restriction sites at the termini.

Each block of the partial sequence is annealed to a complementary partial sequence, and the termini are then cleaved with restriction enzymes that have previously been designed. Thereafter, it was ligated to a suitable vector, and *Escherichia coli* such as *E. coli* DH5α (purchased from Toyobo Co., Ltd.) is then transformed with the obtained vector.

The type of the vector is not particularly limited, as long as it is able to autonomously replicate in *Escherichia coli*. Specific examples of the vector include pBluescript II SK(+)

[Nucleic Acid Research, 17, 9494 (1989)], Lambda ZAP II (manufactured by Stratagene), λgt10, λgt11 [DNA Cloning A Practical Approach, 1, 49 (1985)], pT7T313U (manufactured by Pharmacia), pcD2 [H. Okayama and P. Berg; Mol. Cell. Biol., 3, 280 (1983)], pMW218 (manufactured by Wako Pure Chemical Industries, Ltd.), pUC118, pUC119, pSTV28, pSTV29 (manufactured by Takara Shuzo Co., Ltd.), pEG400 [J. Bac., 172, 2392 (1990)], pHMV1520 (manufactured by MoBiTec)], and pQE-30 (manufactured by QIAGEN).

A plasmid of interest is recovered from the obtained transformant, and it is then cleaved with suitable restriction enzymes. Thereafter, a DNA fragment of the block portion is separated by agarose gel electrophoresis or the like.

The thus obtained DNA fragments are ligated, so as to produce a DNA fragment having the nucleotide sequence as shown in SEQ ID NO: 9. When it is difficult to ligate three or more blocks at a time, a method of successively adding contiguous blocks (FIG. 1) is applied to produce a fragment of interest.

A DNA fragment comprising the nucleotide sequence as shown in SEQ ID NO: 7 can be produced by introducing a mutation into such a fragment. Examples of the mutation introduction method include an error-prone PCR method, a method using hydroxylamine, and a method of allowing a mutation agent such as UV to act on cells having the DNA fragment.

When an error-prone PCR method is used, for example, a plasmid, into which the DNA fragment having the nucleotide sequence as shown in SEQ ID NO: 9 has been incorporated, is used as a template, and a PCR reaction is carried out in a reaction solution wherein a manganese (Mn) salt concentration is higher than usual, using primers as shown in SEQ ID NOS: 34 and 35. The Mn salt concentration may be between approximately 0.1 mmol/l and 1 mmol/l.

4. Method for Producing Protein of the Present Invention

The protein of the present invention can be produced by allowing the DNA of the present invention produced by the method described in 3 above to express in host cells.

In order to allow the DNA to express in host cells, first, the DNA of interest is digested with restriction enzymes, deoxyribonuclease, etc., so as to obtain a DNA fragment with a suitable length that comprises a coding region. Thereafter, the obtained DNA fragment is introduced downstream of a promoter of an expression vector, and the expression vector is then introduced into host cells suitable for the expression vector.

As the host cells, any types of cells can be used, as long as they allow a gene of interest to express therein. Examples of the host cells include bacteria, yeasts, filamentous fungi, animal cells, and plant cells.

As an expression vector, a vector, which is able to autonomously replicate in the aforementioned host cells or can be incorporated into chromosomal DNA, and which comprises a promoter at a position which allows the aformentioned DNA of interest to be transcribed, is used.

When prokaryotes such as bacteria are used as host cells, an expression vector used for expression of the DNA is able to autonomously replicate in the host cells, and is preferably a recombinant vector composed of a promoter, a ribosome-binding sequence, the aforementioned DNA and a transcription termination sequence. A gene for regulating the promoter may also be contained in the expression vector.

Examples of the expression vector include pBTrp2, pBTac1, pBTac2 (all of which are manufactured by Boehringer Mannheim), pKK233-2 (manufactured by Pharmacia), pGEX (manufactured by Pharmacia), pSE280 (manufactured by Invitrogen), pGEMEX-1 (manufactured by Promega), pQE-8 (manufactured by Qiagene), pET-3 (manufactured by Novagen), pKYP10 (Japanese Published Unexamined Patent Application No. 110600/58 (1983)), pKYP200 [Agric. Biol. Chem., 48, 669 (1984)], pLSA1 [Agric. Biol. Chem., 53, 277 (1989)], pGEL1 [Proc. Natl. Acad. Sci., USA, 82, 4306 (1985)], pBluescriptII SK+ (manufactured by Stratagene), pBluescript II SK (−) (manufactured by Stratagene), pTrS30 [prepared from *Escherichia coli* JM109/pTrS30 (FERM BP-5407)], pTrS32 [prepared from *Escherichia coli* JM109/pTrS32 (FERM BP-5408)], pUC19 [Gene, 33, 103 (1985)], pSTV28 (manufactured by Takara Bio Inc.), pUC118 (manufactured by Takara Bio Inc.), pPA1 (Japanese Published Unexamined Patent Application No. 233798/63 (1988)), pEG400 [J. Bacteriol., 172, 2392 (1990)], pHW1520 (manufactured by MoBiTec), and pCS299P (WO 00/63388).

Any type of promoter can be used, as long as it functions in host cells. Examples of the promoter include promoters derived from *Escherichia coli* or phage, such as a trp promoter (Ptrp), a lac promoter (Plac), a $P_L$ promoter, a $P_R$ promoter or a $P_{SE}$ promoter, a SPO1 promoter, a SPO2 promoter, and a penP promoter. In addition, artificially designed or modified promoters such as a promoter formed by placing two Ptrp in series (Ptrp×2), a tac promoter, a lacT7 promoter or a let I promoter, can also be used. Moreover, a xylA promoter for expression in the bacteria of genus *Bacillus*, or a P54-6 promoter for expression in the bacteria of genus *Corynebacterium* can also be used.

It is preferable to use a plasmid wherein the distance between a Shine-Dalgarno sequence that is a ribosome-binding sequence and an initiation codon is appropriately adjusted (for example, 6 to 18 nucleotides).

In the case of the recombinant DNA of the present invention, it is preferable to dispose such a transcription termination sequence directly below a structural gene, while a transcription termination sequence is not always necessary for expression of the DNA of the present invention.

Examples of prokaryotes used as host cells may be microorganisms belonging to genus *Escherichia*, genus *Corynebacterium*, genus *Brevibacterium*, genus *Bacillus*, genus *Microbacterium*, genus *Serratia*, genus *Pseudomonas*, genus *Agrobacterium*, genus *Alicyclobacillus*, genus *Anabaena*, genus *Anacystis*, genus *Arthrobacter*, genus *Azobacter*, genus *Chromatium*, genus *Erwinia*, genus *Methylobacterium*, genus *Phormidium*, genus *Rhodobacter*, genus *Rhodopseudomonas*, genus *Rhodospirillum*, genus *Scenedesmun*, genus *Streptomyces*, genus *Synnecoccus*, genus *Zymomonas*, etc. Preferred examples may be microorganisms belonging to genus *Escherichia*, genus *Corynebacterium*, genus *Brevibacterium*, genus *Bacillus*, etc.

Specific examples of the aforementioned microorganisms include *Escherichia coli* XL1-Blue, *Escherichia coli* XL2-Blue, *Escherichia coli* DH1, *Escherichia coli* DH5α, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Escherichia coli* MP347, *Escherichia coli* NM522, *Bacillus subtilis* ATCC33712, *Bacillus megaterium*, *Bacillus* sp. FERM BP-6030, *Bacillus amyloliquefacines*, *Brevibacterium ammmoniagenes*, *Brevibacterium immariophilum* ATCC14068, *Brevibacterium saccharolyticum* ATCC14066, *Brevibacterium flavum* ATCC14067, *Brevibacterium lactofermentum* ATCC13869, *Corynebacterium glutamicum* ATCC13032, *Corynebacterium glutamicum* ATCC14297, *Corynebacterium acetoacidophilum* ATCC13870, *Corynebacterium ammoniagenes* ATCC6872, *Corynebacterium ammoniagenes* ATCC21264, *Microbacterium ammoniaphilum* ATCC15354, *Serratia*

*ficaria, Serratia fonticola, Serratia liquefaciens, Serratia marcescens, Pseudomonas* sp. D-0110, *Agrobacterium radiobacter, Agrobacterium rhizogenes, Agrobacterium rubi, Anabaena cylindrica, Anabaena doliolum, Anabaena flosaquae, Arthrobacter aurescens, Arthrobacter citreus, Arthrobacter globformis, Arthrobacter hydrocarboglutamicus, Arthrobacter mysorens, Arthrobacter nicotianae, Arthrobacter paraffineus, Arthrobacter protophormiae, Arthrobacter roseoparaffinus, Arthrobacter sulfureus, Arthrobacter ureafaciens, Chromatium buderi, Chromatium tepidum, Chromatium vinosum, Chromatium warmingii, Chromatium fluviatile, Erwinia uredovora, Erwinia carotovora, Erwinia ananas, Erwinia herbicola, Erwinia punctata, Erwinia terreus, Methylobacterium rhodesianum, Methylobacterium extorquens, Phomiidium* sp. ATCC29409, *Rhodobacter capsulatus, Rhodobacter sphaeroides, Rhodopseudomonas blastica, Rhodopseudomonas marina, Rhodopseudomonas palustris, Rhodospirillum rubrum, Rhodospirillum salexigens, Rhodospirillum salinarum, Streptomyces ambofaciens, Streptomyces aureofaciens, Streptomyces aureus, Streptomyces fungicidicus, Streptomyces griseochromogenes, Streptomyces griseus, Streptomyces lividans, Streptomyces olivogriseus, Streptomyces rameus, Streptomyces tanashiensis, Streptomyces vinaceus,* and *Zymomonas mobilis.*

As a method of introducing a recombinant vector into host cells, any type of methods can be used, as long as it is a method of introducing DNA into the aforementioned host cells. Examples of the introduction method for the recombinant vector include a method using calcium ion [Proc. Natl. Acad. Sci. USA, 69, 2110 (1972)], a protoplast method (Japanese Published Unexamined Patent Publication 248394/63 (1988)), an electroporation method, and methods described in Gene, 17, 107 (1982) or Molecular & General Genetics, 168, 111 (1979).

When yeasts are used as host cells, examples of an expression vector used include YEp13 (ATCC37115), YEp24 (ATCC37051), YCp50 (ATCC37419), pHS19, and pHS15.

Any type of promoter can be used, as long as it functions in yeasts. Examples of the promoter include a PHO5 promoter, a PGK promoter, a GAP promoter, an ADH promoter, a gal 1 promoter, a gal 10 promoter, a heat shock protein promoter, an MFa 1 promoter, and a CUP1 promoter.

Examples of yeasts used herein include *Saccharomyces cerevisae, Schizosaccharomyces pombe, Kluyveromyces lactis, Trichosporon pullulans,* and *Schwanniomyces alluvius.*

As a method of introducing a recombinant vector into yeast, any type of method can be used, as long as it is a method of introducing DNA into yeast. Examples of the introduction method for the recombinant vector may include an electroporation method [Methods. Enzymol., 194, 182 (1990)], a spheroplast method [Proc. Natl. Acad. Sci. USA, 75, 1929 (1978)], and a lithium acetate method [J. Bacteriol., 153, 163(1983), Proc. Natl. Acad. Sci. USA, 75, 1929 (1978)].

When animal cells are used as host cells, examples of an expression vector used include pcDNAI, pcDM8 (commercially available from Funakoshi Corp.), pAGE107 [Japanese Published Unexamined Patent Application No. 22979/3 (1991); Cytotechnology, 3, 133, (1990)], pAS3-3 (Japanese Published Unexamined Patent Publication 227075/2 (1990)), pCDM8 [Nature, 329, 840, (1987)], pcDNAI/Amp (manufactured by Invitrogen), pREP4 (manufactured by Invitrogen), pAGE103 [J. Biochem., 101, 1307 (1987)], and pAGE210.

Any type of promoters can be used, as long as it functions in animal cells. Examples of the promoter include a cytomegalovirus (human CMV) IE (immediately early) gene promoter, an SV40 early promoter, a retrovirus promoter, a metallothionein promoter, a heat shock promoter, and a SRα promoter. In addition, a human CMV IE gene enhancer may be used together with the promoter.

Examples of host cells used herein include Namalwa cells, HBT5637 (Japanese Published Unexamined Patent Application No. 299/63 (1988)), COS1 cells, COST cells, and CHO cells.

As a method of introducing a recombinant vector into animal cells, any type of method can be used, as long as it is a method of introducing DNA into animal cells. Examples of the introduction method for the recombinant vector may include an electroporation method [Cytotechnology, 3, 133 (1990)], a calcium phosphate method (Japanese Published Unexamined Patent Application No. 227075/2 (1990)), and a lipofection method [Proc. Natl. Acad. Sci., USA, 84, 7413 (1987), virology, 52, 456 (1973)].

The obtainment and culture of a transformant can be carried out according to methods described in Japanese Published Unexamined Patent Application No. 227075/2 (1990) or Japanese Published Unexamined Patent Application No. 257891/2 (1990).

As an expression method, the protein of the present invention is allowed to directly express, or it can also be expressed in the form of a secretory protein or a fusion protein according to the method described in Molecular Cloning $3^{rd}$ edition or the like.

When the protein of the present invention is allowed to express in yeasts or animal cells, a sugar- or sugar chain-added protein can be obtained.

The aforementioned transformant having the recombinant DNA, into which the DNA of the present invention has been incorporated, is cultured in a medium. Thus, the protein of the present invention is formed and accumulated in the culture, and it is recovered from the culture, so as to produce the protein of the present invention.

The transformant is cultured in a medium according to an ordinary method used in the culture of host cells.

When the transformant is obtained from prokaryotes or microorganisms such as yeasts used as host cells, a medium used for culturing of the microorganisms may be either a natural medium or a synthetic medium, as far as it comprises a carbon source, a nitrogen source, inorganic salts, etc. that can be assimilated by the microorganisms, and it enables an efficient culture of the transformant.

Any type of carbon source can be used, as long as it can be assimilated by microorganisms. Examples of a carbon source used herein include glucose, fructose, sucrose, molasses comprising them, carbohydrates such as starch or starch hydrolysate, organic acids such as acetic acid or propionic acid, and alcohols such as ethanol or propanol.

Examples of a nitrogen source used herein include various types of ammonium salts of inorganic acid or organic acid, such as ammonia, ammonium chloride, ammonium sulfate, ammonium acetate or ammonium phosphate, other nitrogen-containing compounds, peptone, meat extract, yeast extract, corn steep liquor, casein hydrolysate, soybean cake, soybean cake hydrolysate, and various types of fermentative bacterial bodies and the digests thereof.

Examples of an inorganic substance used herein include monopotassium phosphate, dipotassium phosphate, magnesium phosphate, magnesium sulfate, sodium chloride, ferrous sulfate, manganese sulfate, copper sulfate, and calcium carbonate.

Cultivation is performed under aerobic conditions for a shaking cultivation, a submerged cultivation with aeration and agitation, or the like. The cultivation temperature may be between 15° C. and 50° C., and the cultivation time is generally between 16 hours and 7 days. During the cultivation, pH is maintained at pH 3.0 to 9.0. The pH is adjusted using inorganic or organic acid, an alkaline solution, urea, calcium carbonate, ammonia, etc.

In addition, during the cultivation, antibiotics such as ampicillin or tetracycline may be added to the medium, as necessary.

When microorganisms transformed with an expression vector comprising an inducible promoter are cultured, an inducer may be added to the medium, as necessary. For example, when microorganisms transformed with an expression vector comprising a lac promoter are cultured, isopropyl-β-D-thiogalactopyranoside (IPTG) or the like may be added to the medium. When microorganisms transformed with an expression vector comprising a trp promoter are cultured, indoleacrylic acid (IAA) or the like may be added to the medium. When microorganisms transformed with an expression vector comprising a xylA promoter are cultured, xylose may be added to the medium.

Examples of a medium used for culturing a transformant obtained from animal cells used as host cells include a commonly used RPMI1640 medium [The Journal of the American Medical Association, 199, 519 (1967)], Eagle's MEM medium [Science, 122, 501 (1952)], DMEM medium [Virology, 8, 396 (1959)], 199 medium [Proceeding of the Society for the Biological Medicine, 73, 1(1950)], and a medium produced by adding fetal bovine serum to these media.

Cultivation is generally performed for 1 to 7 days under conditions such as pH 6 to 8, a temperature between 30° C. and 40° C., and the presence of 5% $CO_2$.

In addition, during the cultivation, antibiotics such as kanamycin or penicillin may be added to the medium, as necessary.

For isolation and purification of the protein of the present invention from the culture, a common method of isolating and purifying an enzyme may be applied.

For example, when the protein of the present invention is expressed in a soluble form within cells, after completion of the cultivation, the cells are recovered by centrifugation, and are then suspended in an aqueous buffer. Thereafter, the cells are disrupted using an ultrasonic disintegrator, a French press, a Manton Gaulin homogenizer, a Dyno mill, etc., so as to obtain a cell-free extract. A purified sample can be obtained from a supernatant obtained by centrifugation of the aforementioned cell-free extract by performing common enzyme isolation and purification methods, such as a solvent extraction method, a salting-out method using ammonium sulfate, a desalination method, a precipitation method using an organic solvent, an anion exchange chromatography using a resin such as diethylaminoethyl (DEAE)-sepharose or DIAION HPA-75 (manufactured by Mitsubishi Chemical Corp.), cation exchange chromatography using a resin such as S-Sepharose FF (manufactured by Pharmacia), hydrophobic chromatography using a resin such as butyl sepharose or phenyl sepharose, a gel filtration method using a molecular sieve, affinity chromatography, a chromatofocusing method, or electrophoresis such as isoelectric focusing, singly or in combination.

Moreover, when the aforementioned protein is expressed in an insoluble form within cells, the cells are recovered and are then disrupted in the same above manner, followed by centrifugation, so as to obtain a precipitated fraction. Thereafter, the protein is recovered from the precipitated fraction by an ordinary method, and the insoluble protein is solubilized with a protein denaturant. The solubilized solution is diluted or dialyzed with a solution that contains no protein denaturants, or with a solution that contains a protein denaturant whose concentration is too low to denature the protein, so that the protein is allowed to have a normal three-dimensional structure. Thereafter, the same isolation and purification methods as described above are applied to the protein, so as to obtain a purified sample.

When the protein of the present invention or a derivative thereof such as a sugar-modified derivative thereof is secreted outside the cells, the protein or a derivative thereof such as a sugar chain-added derivative thereof can be recovered from the culture supernatant. That is to say, the culture is treated by the aforementioned methods such as centrifugation, so as to obtain a soluble fraction. Thereafter, a purified sample can be obtained from the soluble fraction by the same isolation and purification methods as described above.

Examples of the thus obtained protein include proteins having the amino acid sequences as shown in SEQ ID NOS: 1 to 3. In addition, the protein expressed by the aforementioned method can also be produced by chemical synthesis methods such as an Fmoc method (fluorenylmethyloxycarbonyl method) or a tBoc method (t-butyloxycarbonyl method). Moreover, the aforementioned protein can also be synthesized using peptide synthesizers available from the following distributors: Sowa Trading Co., Inc. (manufactured by Advanced ChemTech, U.S.A.), Perkin-Elmer Japan (manufactured by Perkin-Elmer, U.S.A.), Pharmacia Biotech (manufactured by Pharmacia Biotech, Sweden), ALOKA Co., Ltd. (Protein Technology Instrument, U.S.A.), Kurabo Industries Ltd. (manufactured by Synthecell-Vega, U.S.A.), Nihon PerSeptive Ltd. (manufactured by PerSeptive, U.S.A.), and Shimadzu Corp.

5. Method for Producing Compound (II-a) or Compound (II-b)

Cells obtained by the culture according to the method described in 4 above, a culture of the cells, treated cells, or the purified protein of the present invention is allowed to come into contact with the compound (I-a) or the compound (I-b) in a medium, so as to form and accumulate compound (II-a) or (II-b) in the medium. Thereafter, the compound (II-a) or the compound (II-b) is recovered from the medium, thereby producing the compound (II-a) or the compound (II-b).

Examples of a treated culture of the cells of the present invention include a concentrated culture, a dried culture, a freeze-dried culture, and a treated product that maintains the form of the cells, such as cells obtained from the culture by centrifugation, dried cells, freeze-dried cells, surfactant-treated cells, enzyme-treated cells, solvent-treated cells and immobilized cells, and a crude enzyme extract such as ultrasonic-treated cells and a mechanically crushed cells, and a roughly purified enzyme such as a protein fraction from the cells and an immobilized product of the enzyme.

As a medium, water, an aqueous medium, an organic solvent, or a mixed solution consisting of water or an aqueous medium and an organic solvent, is used. Examples of the aqueous medium used herein include buffer solutions such as a phosphate buffer, a HEPES (N-2-hydroxyethylpiperazin-N-ethanesulfonic acid) buffer, or a Tris [Tris(hydroxymethyl)aminomethane]-HCl buffer. Any type of organic solvent may be used, as long as it does not inhibit the reaction. Examples of the organic solvent include acetone, ethyl acetate, dimethyl sulfoxide, xylene, methanol, ethanol, and butanol. A mixed solution consisting of water or an aqueous medium and an organic solvent is preferably used when the compound (I-b) is used, for example. In addition, as an aqueous medium, a culture solution used in the cultivation of the cells of the present invention and the culture solution obtained as a result of the cultivation can also be used.

When the compound (I-a) or the compound (I-b) is added to a medium, the compound (I-a) or the compound (I-b) may be dissolved in water, an aqueous medium or an organic solvent, or a mixed solution consisting of water or an aqueous medium and an organic solvent, which can dissolve the aforementioned compounds, and the obtained solution may be then added to the medium. Any type of organic solvent can be used, as long as it does not inhibit the reaction. Examples of the organic solvent include acetone, ethyl acetate, dimethyl sulfoxide, xylene, methanol, ethanol, and butanol.

When a culture solution used in the cultivation of the cells of the present invention is used as a medium, the compound (I-a) or the compound (I-b) may previously be added to the culture solution before initiation of the cultivation, or the compound (I-a) or the compound (I-b) may also be added to the solution during the cultivation or after completion of the cultivation.

When the compound (I-a) or the compound (I-b) is added to the culture solution, 0.1 to 10 mg of, and preferably 0.2 to 1 mg of the compound (I-a) or the compound (I-b) is added to 1 ml of a medium before initiation of the culture or at the mid-course of the culture. It is preferable that the compound (I-a) or the compound (I-b) is first dissolved in water or an organic solvent such as methanol or ethanol, and is then added to the culture solution.

In the method for producing the compound (II-a) or compound (II-b) of the present invention, the amount of an enzyme source used differs depending on the specific activity or the like. When the culture of the cells or a treated culture of the cells is used as an enzyme source, for example, 5 to 1,000 mg (wet weight) of, and preferably 10 to 400 mg (wet weight) of enzyme is added to 1 mg of the compound (I-a) or the compound (I-b). The reaction is carried out at a temperature preferably between 20° C. and 50° C., and particularly preferably between 25° C. and 37° C. The reaction time differs depending on the amount of an enzyme source used, specific activity, etc. It is generally between 2 and 150 hours, and preferably 6 to 120 hours.

The compound (I-b) and the compound (II-b) can easily be converted to the compound (I-a) and the compound (II-a), respectively, by the below-mentioned lactone ring-opening method. Also, the compound (I-a) and the compound (II-a) can easily be converted to the compound (I-b) and the compound (II-b), respectively, by the below-mentioned lactone forming method.

As a method of opening a lactone ring, there is a method comprising dissolving the compound (I-b) or the compound (II-b) in an aqueous medium and then adding acid or alkali thereto to open the ring. Examples of the aqueous medium include aqueous solutions comprising salts that do not inhibit the reaction, such as water, a phosphate buffer, or a Tris buffer. The aqueous solution may comprise organic solvents such as methanol, ethanol, or ethyl acetate, in a concentration that does not inhibit the reaction. Examples of acid include acetic acid, hydrochloric acid, and sulfuric acid. Examples of alkali include sodium hydroxide, potassium hydroxide, and ammonia.

As a method of forming a lactone, there is a method comprising dissolving the compound (I-a) or the compound (II-a) in a nonaqueous medium and then adding acid or a base catalyst thereto to form a lactone. As a nonaqueous solvent, any type of nonaqueous solvent can be used, as long as it is an organic solvent that does not substantially contain water and is able to dissolve the compound (I-a) or the compound (II-a). Examples of the solvent include dichloromethane and ethyl acetate. As a catalyst, any type of catalyst can be used, as long as it catalyzes a lactonization reaction and it has no action other than lactonization on a substrate or a reaction product. Examples of the catalyst include trifluoroacetic acid and para-toluenesulfonic acid. The reaction temperature is not particularly limited. It is preferably between 0° C. and 100° C., and particularly preferably between 20° C. and 80° C.

The compound (II-a) and the compound (II-b) can be recovered from the medium by methods used in common organic synthetic chemistry, such as extraction with an organic solvent, crystallization, thin-layer chromatography, or high performance liquid chromatography.

As a method of confirming or quantifying the compound (II) produced by the method of the present invention, any type of method can be used, as long as the compound (II), preferably the compound (II-a) and/or the compound (II-b) can be confirmed or quantified. Examples of the method include $^{13}$C-NMR spectrum, $^1$H-NMR spectrum, mass spectrum, and high performance liquid chromatography (HPLC).

6. Definition of Each Group of Compound of the Present Invention

In each group of the compounds represented by Formulas (I) to (IX), (XI), (XIII) and (XV), alkyl is linear or branched alkyl having 1 to 10 carbon atoms, and preferably 1 to 6 carbon atoms. Examples of alkyl include methyl, ethyl, propyl, isopropyl, butyl, isobutyl, sec-butyl, tert-butyl, pentyl, neopentyl, hexyl, isohexyl, heptyl, 4,4-dimethylpentyl, octyl, 2,2,4-trimethylpentyl, nonyl, decyl, and various types of branched chain isomers thereof.

Examples of aryl include phenyl and naphthyl.

Examples of a substituent in substituted alkyl include 1 to 3 identical or different halogen atoms, hydroxyl groups, amino groups, alkoxy groups, and aryl groups.

Examples of a substituent in substituted aryl include 1 to 3 identical or different halogen atoms, hydroxyl groups, amino groups, alkyl groups, and alkoxy groups.

Examples of halogen include fluoro, chloro, bromo, and iodo.

An alkyl portion in alkoxy has the same definitions as those of alkyl described above.

An aryl group in substituted alkyl has the same definitions as those of aryl described above.

An alkyl group in substituted aryl has the same definitions as those of alkyl described above.

The term "alkali metal" is used herein to mean elements such as lithium, sodium, potassium, rubidium, cesium, and francium.

The present invention will be described in the following reference examples and examples. However, these examples are not intended to limit the scope of the present invention.

Reference Example

Production of Vector Plasmid

A plasmid pFM54-6 (Appl. Microbiol. Biotechnol., 53, 674-679, 2000) comprising a promoter region derived from *Corynebacterium ammoniagenes* was used as a template, and DNA having the nucleotide sequence as shown in SEQ ID NO: 36 and DNA having the nucleotide sequence as shown in SEQ ID NO: 37 were used as primers. Using such a template and such primers, PCR was carried out, so as to amplify a 0.7-kb DNA fragment comprising a promoter region. This fragment was cleaved with EcoRV and BamHI, and it was then inserted into the HincII-BamHI region of a commercially available *Escherichia coli* vector pTZ18R (Protein Engineering, 1, 67-74, 1986), so as to obtain a plasmid pRI107. This plasmid was cleaved with PstI and BamHI, and the obtained PstI-BamHI DNA fragment having a size of approximately 0.7 kb was introduced into the Sse8387I-BamHI region of pCS299P (WO00/63388), so as to obtain pRI109.

Example 1

Preparation of Reaction Substrate 100 mg of compound (VII-b) (manufactured by Sigma) was dissolved in 9.5 ml of methanol, and 0.5 ml of 1 mol/l sodium hydroxide was then added thereto. The mixture was shaken at room temperature for 1 hour. The obtained reaction solution was dried, and 5 ml of deionized water was then added thereto for dissolution. Thereafter, using approximately 0.1 ml of 1 mol/l hydrochloric acid, the pH of the solution was adjusted to approximately pH 6.5 to 7.5. Thereafter, 4.9 ml of deionized water was further added to the solution, so as to obtain 10 ml of compound (VII-a) having a final concentration of 10 mg/ml [which was a compound wherein, in Formula (XIII), $R^1$ represents sodium].

Example 2

Obtainment of pRIyjiB and pSYN2-39

Using pWyjiB (WO 00/44886, and the corresponding U.S. Pat. No. 7,049,111 and EP1148122) as a template, and also using DNA having the nucleotide sequence as shown in SEQ ID NO: 38 and DNA having the nucleotide sequence as shown in SEQ ID NO: 39 as a primer set, PCR was carried out.

As a PCR reaction, incubation was performed at 96° C. for 1 minute, and thereafter, a cycle consisting of 95° C.—30 seconds, 50° C.—45 seconds and 72° C.—3 minutes was repeated 25 times Thereafter, incubation was performed at 72° C. for 10 minutes. By such PCR, an amplified DNA fragment having a size of approximately 1.4 kb was obtained. The DNA fragment was cleaved with SalI and BamHI, and it was then ligated to pRI109 that had also been cleaved with SalI and BamHI.

The thus ligated recombinant DNA was introduced into *Escherichia coli* DH5α by the electroporation method. The obtained plasmid was isolated from the *Escherichia coli*, and it was then introduced into a *C. glutamicum* ATCC13032 strain by the electroporation method. With regard to each of the obtained 10 transformant strains, the activity of converting the compound (VII-a) to compound (VIII-a) was measured as follows.

That is to say, each strain was inoculated into a test tube containing 3 ml of a KM102 medium (2% bouillon and 0.5% yeast extract) comprising 100 μg/ml kanamycin, and it was then cultured at 30° C. overnight. 0.5 ml out of the obtained culture was added to a test tube containing 5 ml of an LMC medium [3% glucose, 0.1% $NH_4Cl$, 0.1% $KH_2PO_4$, 0.3% $K_2HPO_4$, 0.01% $MgSO_4.7H_2O$, 0.05% yeast extract, 1% corn steep liquor, 2 mg/l $FeSO_4$, 2 mg/l $MnSO_4$, 50 μg/l biotin, and 0.5 mg/l thiamine (pH7.2)] comprising 100 μg/ml kanamycin, followed by a shaking clutivation at 30° C. for 5 hours. Thereafter, the compound (VII-a) prepared in Example 1 was added to the reaction solution to a final concentration of 500 mg/l, and the obtained mixture was further subjected to a shaking cultivation at 30° C. for 6 hours.

0.5 ml out of the obtained culture was transferred into a 1.5-ml tube, and it was then centrifuged at 15,000 rpm for 2 minutes to separate a cell mass. The obtained supernatant portion was 5 to 20 times diluted with methanol, and the thus diluted solution was then centrifuged at 15,000 rpm for 2 minutes. A portion of the centrifuged product was subjected to HPLC analysis [column: Inertsil ODS-2 (5 μm, 4×250 mm, manufactured by GL Sciences); column temperature: 60° C.; mobile phase:acetonitrile:water:phosphoric acid=55:45: 0.05; flow rate: 0.9 ml/min; detection wavelength: 237 nm], so as to quantify the compound (VIII-a) (which was a compound wherein, in Formula (XV), $R^1$ represents sodium). A strain having the highest conversion activity [the amount of the compound (VIII-a) formed: 56 mg/l, conversion ratio: 16%] was selected, and this strain was named as ATCC13032/pRIyjiB.

Based on a plasmid pRIyjiB extracted from the aforementioned strain, the distance between an SD sequence and an initiation codon was further optimized. The $2^{nd}$, $3^{rd}$, $4^{th}$, and $7^{th}$ codons on the N-terminal side of the yjiB gene were substituted with codons that were suitable for *C. glutamicum*, so as to produce an expression plasmid.

Subsequently, using pRIyjiB as a template, and also using DNAs having the nucleotide sequences as shown in SEQ ID NOS: 40 and 39 as a primer set, PCR was carried out. As a PCR reaction, incubation was performed at 96° C. for 1 minute, and thereafter, a cycle consisting of 95° C.—30 seconds, 50° C.—45 seconds and 72° C.—3 minutes was repeated 25 times. Thereafter, incubation was performed at 72° C. for 10 minutes. By such PCR, an amplified DNA fragment having a size of approximately 1.4 kb was obtained.

The DNA fragment was cleaved with XhoI and BamHI, and it was then ligated to pRI109 that had also been cleaved with SalI and BamHI, so as to obtain recombinant DNA. The recombinant DNA was introduced into *Escherichia coli* DH5α by the electroporation method, so as to obtain a transformant. A plasmid was isolated from the transformant, and it was then introduced into a *C. glutamicum* ATCC 13032 strain by the electroporation method.

The obtained 30 transformant strains were cultured in the same above manner, and with regard to each of the 30 transformant strains, the activity of converting the compound (VII-a) to the compound (VIII-a) was measured. A strain having the highest conversion activity [the amount of the compound (VIII-a) formed: 80 mg/l, conversion ratio: 28%] was selected. A plasmid owned by the selected strain was named as pSYN2-39, and the strain was named as ATCC13032/pSYN2-39.

Example 3

Separation of Mutation Points Using Restriction Enzymes

With regard to the pRIyjiB and the pSYN2-39 obtained in Example 2, the nucleotide sequences of the coding regions of yjiB genes were determined. As a result, it was found that 2 nucleotides of the nucleotide sequence of pRIyjiB were different from those of the known yjiB gene, and that 8 nucleotides of the nucleotide sequence of pSYN2-39 was different from those of the known yjiB gene. Such mutations are shown in Table 1. Hereafter, the position of a nucleotide will be expressed by defining A of the translation initiation codon ATG as 1, and the position of an amino acid residue will be expressed by defining Met at the N-terminus of a protein encoded by the yjiB gene (Met at position 1 of the amino acid sequence as shown in SEQ ID NO: 4) as 1.

TABLE 1

| Nucleotide | | | | Amino acid | | | Mutant |
|---|---|---|---|---|---|---|---|
| Position | Wild type | pRIyjiB | pSYN2-39 | Position | Wild type | pRIyjiB | pSYN2-39 | name |
| 32  | A | A | C | 11  | Q | Q | P | Q11P |
| 248 | A | A | G | 83  | N | N | S | N83S |
| 311 | T | C | C | 104 | V | A | A | V104A |
| 404 | T | T | A | 135 | F | F | Y | F135Y |
| 696 | T | G | G | 232 | F | L | L | F232L |
| 758 | A | A | T | 253 | Y | Y | F | Y253F |
| 819 | T | T | C | 273 | P | P | P | 819 |
| 926 | T | T | C | 309 | M | M | T | M309T |

The influence of such mutations on conversion activity was examined.

First, a non-mutant yjiB gene having the same structure as pSYN2-39 was inserted into pRI109, so as to produce a plasmid. The chromosomal DNA (WO 00/44886) of a *Bacillus subtilis* 168 strain was used as a template, and DNAs having the nucleotide sequences as shown in SEQ ID NOS: 38 and 39 were used as a primer set. Using such a template and such a primer set, PCR was carried out. As a PCR reaction, incubation was performed at 96° C. for 1 minute, and thereafter, a cycle consisting of 95° C.—30 seconds, 50° C.—45 seconds and 72° C.—3 minutes was repeated 25 times. Thereafter, incubation was performed at 72° C. for 10 minutes. By such PCR, an amplified DNA fragment having a size of approximately 1.2 kb was obtained.

The DNA fragment was ligated to pT7Blue (manufactured by Novagen) to obtain recombinant DNA, and the obtained recombinant DNA was then introduced into *Escherichia coli* DH5α by the electroporation method. A plasmid was extracted from the obtained transformant, and the nucleotide sequence of the coding region of the yjiB gene was determined, so as to confirm that there were no mutations.

The plasmid was cleaved with SalI and BamHI, and the obtained approximately 1.2-kb DNA fragment comprising yjiB was then ligated to each of pRI109 and pBluescriptII SK+ that had been cleaved with SalI and BamHI, so as to obtain recombinant DNAs. The obtained recombinant DNAs were named as pN9 and pN9SK, respectively.

The ClaI-BamHI portion of pN9SK was substituted with the corresponding portion of pRIyjiB to produce pN5SK, and the SalI-BamHI portion of pN5SK was introduced into pRI109 to produce pN5.

Subsequently, using pSYN2-39 as a template, and also using DNAs having the nucleotide sequences as shown in SEQ ID NOS: 40 and 39 as a primer set, PCR was carried out, so as to amplify an yjiB region. The obtained 1.2-kb DNA fragment was ligated to pT-Blue (manufactured by Novagen), so as to obtain recombinant DNA. The nucleotide sequence of the recombinant DNA was determined, and it was confirmed that the recombinant DNA had a mutation that pSYN2-39 had. Thereafter, the SalI-BamHI fragment of the recombinant DNA was ligated to each of pRI109 and pBluescriptII SK+, so as to obtain recombinant DNAs. The obtained recombinant DNAs were named as pN1 and pN1 SK, respectively.

Subsequently, the ClaI-BamHI fragment or EcoRI-BamHI fragment of pN1SK, pN5SK and pN9SK was substituted with each other, so as to obtain plasmids named as pN1C9SK, pN9C1SK, pN1E9SK and pN9E1SK. The SalI-BamHI fragment comprising the yjiB portion of such plasmids was introduced into pRI109, so as to obtain plasmids named as pN1C9, pN9C1, pN1C5, pN1E9 and pN9E1.

Moreover, the DraI-BamHI regions of pN1, pN5 and pN9 were substituted with the corresponding regions of pN1SK, pN5SK and pN9SK, so as to obtain plasmids named as pN1D9, pN1D5, pN9D1 and pN5D9. Furthermore, the DraI-BamHI regions of pN1C9 and pN1C5 were substituted with pN1, so as to obtain plasmids named as pN1C9D1 and pN1C5D1.

Still further, the EcoRI-BamHI fragments of pN1C9SK and pN1C5SK were substituted with pN1, so as to obtain plasmids named as pN1C9E1SK and pN1C5E1. The SalI-BamHI fragments comprising the yjiB portions of the plasmids were introduced into pRI109, so as to obtain plasmids named as pN1C9E1 and pN1C5E1.

The positional relationship between mutation points existing in the yjiB gene-corresponding portions of the aforementioned plasmids and restriction sites is shown in FIG. 2.

Each of the thus obtained pN1, pN5, pN9, pN1C9, pN1C5, pN1E9, pN1D9, pN1D5, pN9C1, pN9E1, pN9D1, pN5D9, pN1C9D1, pN1C5D1, pN1C5E1 and pN1C9E1 was introduced into *C. glutamicum* ATCC13032 by the electroporation method. The obtained transformants were cultured by the same method as that described in Example 2, and the activities of converting the compound (WII-a) to the compound (VIII-a) were then measured. The results are shown in Table 2.

TABLE 2

| | Mutation point | | | | | | | | Consumed compound (VII-a) | Generated compound (VIII-a) | Conversion |
|---|---|---|---|---|---|---|---|---|---|---|---|
| Plasmid | Q11P | N83S | V104A | F135Y | F232L | Y253F | 819 | M309T | (mg/l) | (mg/l) | ratio (%) |
| pN9     | —  | —  | —  | —  | —  | —  | —  | —  | 125 | 29  | 23.2 |
| pN1     | ◯  | ◯  | ◯  | ◯  | ◯  | ◯  | ◯  | ◯  | 409 | 174 | 42.5 |
| pN5     | —  | —  | ◯  | —  | ◯  | —  | —  | —  | 463 | 83  | 17.9 |
| pN1C9   | ◯  | —  | —  | —  | —  | —  | —  | —  | 141 | 55  | 39.0 |
| pN1C5   | ◯  | —  | ◯  | —  | ◯  | —  | —  | —  | 418 | 138 | 33.0 |
| pN1E9   | ◯  | ◯  | ◯  | —  | —  | —  | —  | —  | 141 | 49  | 34.8 |
| pN1D9   | ◯  | ◯  | ◯  | ◯  | —  | —  | —  | —  | 374 | 93  | 24.9 |
| pN1D5   | ◯  | ◯  | ◯  | ◯  | ◯  | —  | —  | —  | 415 | 127 | 30.6 |

TABLE 2-continued

| Plasmid | Mutation point | | | | | | | | Consumed compound (VII-a) (mg/l) | Generated compound (VIII-a) (mg/l) | Conversion ratio (%) |
|---|---|---|---|---|---|---|---|---|---|---|---|
| | Q11P | N83S | V104A | F135Y | F232L | Y253F | 819 | M309T | | | |
| pN9C1 | — | ○ | ○ | ○ | ○ | ○ | ○ | ○ | 426 | 80 | 18.8 |
| pN9E1 | — | — | — | ○ | ○ | ○ | ○ | ○ | 456 | 104 | 22.8 |
| pN9D1 | — | — | — | — | ○ | ○ | ○ | ○ | 219 | 48 | 21.9 |
| pN5D9 | — | — | ○ | — | — | — | — | — | 231 | 43 | 18.6 |
| pN1C9D1 | ○ | — | — | — | ○ | ○ | ○ | ○ | 114 | 64 | 56.1 |
| pN1C5D1 | ○ | — | ○ | — | ○ | ○ | ○ | ○ | 445 | 175 | 39.3 |
| pN1C5E1 | ○ | — | ○ | ○ | ○ | ○ | ○ | ○ | 438 | 182 | 41.6 |
| pN1C9E1 | ○ | — | — | ○ | ○ | ○ | ○ | ○ | 431 | 197 | 45.7 |

Mutation point: In the above table, ○ indicates that the plasmid comprises a mutation of the amino acid residue shown in the upper case, and — indicates that the plasmid does not comprise such a mutation.
Consumed compound (VII-a): the value obtained by subtracting the amount of the remaining compound (VII-a) after completion of the reaction from the additive amount (500 mg/l)
Conversion ratio: The amount of the formed compound (VIII-a) with respect to the amount of the consumed compound (VII-a)

As shown in Table 2, it was found that 8 mutations had the effect of changing a conversion ratio and a conversion speed in the reaction of converting the compound (VII-a) to the compound (VIII-a) by the yjiB gene products, and that additive action was observed regarding such mutation effects.

For example, when compared with wild-type yjiB(pN9), pN1C9 comprising a Q11P mutation shows a higher conversion ratio. Thus, it is found that this mutation has the effect of increasing a conversion ratio. On the other hand, pN5 has V104A and F232L mutations, and the amount of the compound (VIII-a) formed in pN5 is larger than that of pN9. Thus, it is found that pN5 has the effect of increasing a conversion speed. In the case of pN1C5, which has the aforementioned two types of mutations, it has both the characteristics, namely, a high conversion ratio and a high conversion speed.

As another example, when pN1C9 is compared with pN1E9, both the conversion speed and the conversion ratio are somewhat lower. Thus, it is considered that both or either of N83S and V104A contained in pN1E9 is a harmful mutation. On the other hand, the conversion rate of pN5D9 only comprising a V104A mutation is somewhat lower than that of the wild type, but its conversion speed is improved. Accordingly, it is assumed that N83S is a harmful or invalid mutation. In fact, pN1C5E, wherein only the N83S mutation was excluded from pN1, had results equivalent to the results of pN1.

Example 4

Preparation of pSYN2-39cod

As described below, the codon in a coding region corresponding to the yjiB gene of pSYN2-39 was substituted with a codon suitable for expression in *Corynebacterium*.

First, the sequences as shown in SEQ ID NOS: 10 to 33 were synthesized using a DNA synthesizer.

Next, a DNA fragment with a size of approximately 200 by obtained by annealing DNAs having the nucleotide sequences as shown in SEQ ID NOS: 10 to 13 was digested with SalI and HindIII, and it was then introduced into the SalI site of a commercially available *Escherichia coli* vector pUC119, so as to obtain pSC1. Moreover, a DNA fragment with a size of approximately 280 by obtained by annealing DNAs having the nucleotide sequences as shown in SEQ ID NOS: 14 to 19 was digested with SphI and Hindu, and it was then inserted into the SphI-HindIII site of pSC1, so as to obtain pSC2.

Furthermore, a DNA fragment with a size of approximately 200 by obtained by annealing DNAs having the nucleotide sequences as shown in SEQ ID NOS: 20 to 23 was digested with SalI and BamHI, and it was then introduced into the SalI-BamHI site of pUC119, so as to obtain pSC3. Still further, a DNA fragment with a size of approximately 200 by obtained by annealing DNAs having the nucleotide sequences as shown in SEQ ID NOS: 24 to 27 was digested with SalI and EcoRV, and it was then introduced into the SalI-EcoRV site of pSC3, so as to obtain pSC4. Further, a DNA fragment with a size of approximately 200 by obtained by annealing DNAs having the nucleotide sequences as shown in SEQ ID NOS: 28 to 33 was digested with SalI and Eco81I, and it was then introduced into the SalI-Eco81I site of pSC4, so as to obtain pSC5.

Finally, pSC2 was digested with SalI and BglII, and the obtained DNA fragment with a size of approximately 490 by was then introduced into the SalI-BamHI site of pSC5, so as to produce a plasmid pSC6 having an approximately 1.2-kb insertion sequence at the SalI-BamHI site of pUC119. The production process of pSC6 is as shown in FIG. 1.

The pSC6 was digested with BamHI and SalI. Thereafter, an approximately 1.2-kb DNA was obtained, and it was then ligated to pRI109 that had been digested with BamHI and SalI, so as to obtain pSYN2-39cod.

The pSYN2-39cod was introduced into a *Corynebacterium ammoniagenes* ATCC21264 strain by the electroporation method (WO 00/44886).

The obtained transformant strain was named as *C. ammoniagenes* ATCC21264/pSYN2-39cod. The activity of converting the compound (VII-a) to the compound (VIII-a) was measured as follows.

That is to say, *C. ammoniagenes* ATCC21264/pSYN2-39cod was inoculated into a test tube containing 3 ml of an ASB medium [5% glucose, 0.5% $(NH_4)_2SO_4$, 0.1% $KH_2PO_4$, 0.1% $K_2HPO_4$, 0.1% $MgSO_4.7H_2O$, 1% yeast extract, 1% polypeptone, 0.1% urea, 20 mg/l $FeSO_4$, 40 mg/l $MnSO_4$, 10 mg/l $ZnSO_4$, 2 mg/l $CuSO_4$, 20 mg/l L-cysteine hydrochloride, 15 mg/l β alanine, 100 mg/l biotin, 15 mg/l thiamine, 100 mg/l adenine, 100 mg/l guanine (pH 7.2)] comprising 100 µg/ml kanamycin. The obtained mixture was subjected to a shaking cultivation at 30° C. overnight. 0.2 ml out of the obtained culture was added to a test tube containing 1.8 ml of an APB medium [4% glucose, 0.35% $(NH_4)_2SO_4$, 0.43% $KH_2PO_4$, 1.45% $K_2HPO_4$, 0.4% $MgSO_47H_2O$, 2% corn steep liquor, 10 mg/l $FeSO_4$, 4 mg/l $MnSO_4$, 20 mg/l $ZnSO_4$, 0.5 mg/l $CuSO_4$, 20 mg/l L-cysteine hydrochloride, 10 mg/l calcium pantothenate, 60 µg/l biotin, 15 mg/l thiamine, 90 mg/l adenine, and 90 mg/l guanine (pH 7.2)] comprising 100 µg/ml kanamycin. The obtained mixture was subjected to a shaking culture at 30° C. for 5 hours. Thereafter, the compound (VII-b) prepared in Example 1 was added to the reaction solution to a final concentration of 500 mg/l, and the mixture was further subjected to a shaking cultivation at 30° C. for 20 hours. Thereafter, the amounts of the compound (VIII-a) and the compound (VII-a) contained in the obtained culture solution were measured in the same manner as that in Example 2 (Table 3).

The DNA fragment was cleaved with SalI and BamHI, and it was then ligated to a vector portion of pSYN2-39cod that had also been cleaved with SalI and BamHI, so as to produce recombinant DNA. The recombinant DNA was introduced into *Escherichia coli* DH10B by the electroporation method.

The colonies of the obtained transformant strain were individually cultured in an LB medium (1% bactotryptone, 0.5% yeast extract, and 1% NaCl) using a 96-well titer plate. Thereafter, the culture products were mixed, and a plasmid was then extracted by the alkaline method. This plasmid having a ran-

TABLE 3

| Plasmid | Mutation point | | | | | | | | | |
|---|---|---|---|---|---|---|---|---|---|---|
| | L14P | N16I | G17V | K18R | K35M | S83N | F123L | V132G | V143G | H154R |
| pSYN2-39cod | — | — | — | — | — | — | — | — | — | — |
| pEP77 | ○ | ○ | — | ○ | — | — | ○ | ○ | — | ○ |
| pEP129 | ○ | ○ | — | — | — | — | — | — | — | ○ |
| pEP139 | — | — | — | — | — | — | — | — | — | — |
| pEP268 | — | — | ○ | — | ○ | — | — | — | — | — |
| pES346 | — | — | ○ | — | — | — | — | — | ○ | — |
| pES509 | — | — | ○ | — | ○ | — | — | — | ○ | — |
| pES709 | — | — | ○ | — | ○ | — | — | — | ○ | — |
| pES849 | ○ | ○ | — | — | — | — | — | — | ○ | ○ |
| pES78-1 | — | — | ○ | — | — | Δ | — | — | ○ | — |
| pES849-1 | ○ | ○ | — | — | — | Δ | — | — | ○ | ○ |
| pES503-1 | — | — | ○ | — | — | Δ | — | — | ○ | ○ |

| Plasmid | Mutation point | | | | | Consumed compound (VII-a) (mg/l) | Generated compound (VIII-a) (mg/l) | Conversion ratio (%) |
|---|---|---|---|---|---|---|---|---|
| | C187Y | A284T | E306G | G343A | L357P | | | |
| pSYN2-39cod | — | — | — | — | — | 290.3 | 54.3 | 18.6 |
| pEP77 | — | ○ | — | — | ○ | 445.5 | 188.9 | 42.4 |
| pEP129 | — | — | — | — | — | 478.1 | 257.5 | 53.9 |
| pEP139 | — | — | — | ○ | — | 380.3 | 179.9 | 47.3 |
| pEP268 | ○ | ○ | ○ | — | — | 431.1 | 130.2 | 30.2 |
| pES346 | ○ | ○ | ○ | ○ | — | 491.7 | 301.4 | 61.3 |
| pES509 | — | ○ | — | ○ | — | 500.0 | 271.8 | 54.4 |
| pES709 | — | — | — | ○ | — | 498.9 | 235.3 | 47.1 |
| pES849 | — | ○ | ○ | ○ | — | 453.7 | 280.4 | 61.8 |
| pES78-1 | ○ | ○ | ○ | ○ | — | 483.7 | 301.4 | 62.3 |
| pES849-1 | — | ○ | ○ | ○ | — | 450.0 | 280.4 | 62.8 |
| pES503-1 | — | ○ | ○ | ○ | — | 478.7 | 305.4 | 63.8 |

Mutation point: In the above table, ○ indicates that the plasmid comprises a mutation of the amino acid residue shown in the upper case, — indicates that the plasmid does not comprise such a mutation, and Δ indicates that the plasmid comprises a mutation that has been newly introduced by PCR.
Consumed compound (VII-a): the value obtained by subtracting the amount of the remaining compound (VII-a) after completion of the reaction from the additive amount (500 mg/l)
Conversion ratio: The amount of the formed compound (VIII-a) with respect to the amount of consumed compound (VII-a)

Example 5

Preparation of First-Generation Mutant Gene

In order to increase the conversion ratio of *C. ammoniagenes* ATCC21264/pSYN2-39cod of converting the compound (VII-a) to the compound (VIII-a), a mutation was introduced into the coding region of a gene corresponding to the yjiB gene contained in pSYN2-39cod by the error-prone PCR method.

That is, using pSC6 as a template, and also using the nucleotide sequences as shown in SEQ ID NOS: 41 and 42 as a primer set, PCR was carried out in a reaction solution comprising 0.3 mmol/l MnCl2. As a PCR reaction, incubation was performed at 96° C. for 1 minute, and thereafter, a cycle consisting of 95° C.—30 seconds, 58° C.—30 seconds and 72° C.—2 minutes was repeated 25 times. Thereafter, incubation was performed at 72° C. for 10 minutes. By such PCR, a DNA fragment, wherein a mutation had randomly been introduced into a DNA portion with a size of approximately 1.2 kb, was obtained.

dom mutant gene was introduced into a *C. ammoniagenes* ATCC21264 strain by the electroporation method, so as to produce a recombinant strain library having random mutation-introduced genes.

Each strain in the aforementioned library was cultured by the method described in Example 4, and the conversion activity thereof of converting the compound (VII-a) to the compound (VIII-a) was measured. Several thousands of strains were subjected to a reaction test, and four strains exhibiting a high conversion activity were selected from such strains. The plasmids of the four strains were named as pEP77, pEP129, pEP139, and pEP268. The test results regarding the four strains are shown in the above Table 3.

As shown in Table 3, when compared with the pSYN2-39cod-containing strain, both the conversion speed and the conversion ratio were significantly improved. Each of such pEP77, pEP129, pEP139, and pEP268 was isolated, and the nucleotide sequence of a coding region corresponding to the yjiB gene portion was determined. Each plasmid has a mutation to pSYN2-39cod, as shown in Table 4.

TABLE 4

| Mutated site | Base change Gene sequence on pSYN2-39cod → | Sequence of mutant gene | Amino acid change | pEP77 | pEP129 | pEP139 | pEP268 |
|---|---|---|---|---|---|---|---|
| 41 | T | C | L14P | ○ | ○ | | |
| 47 | A | T | N16I | ○ | ○ | | |
| 50 | G | T | G17V | | | | ○ |
| 53 | A | G | K18R | ○ | | | |
| 104 | A | T | K35M | | | | ○ |
| 367 | T | C | F123L | ○ | | | |
| 395 | T | G | V132G | ○ | | | |
| 428 | T | G | V143G | | | | ○ |
| 461 | A | G | H154R | ○ | ○ | | |
| 560 | G | A | C187Y | | | | ○ |
| 850 | G | A | A284T | ○ | | | ○ |
| 917 | A | G | E306G | | | | ○ |
| 1028 | G | C | G343A | | | ○ | |
| 1070 | T | C | L357P | ○ | | | |

As shown in Table 4, it became clear that the mutations of pEP77, pEP129, pEP139 and pEP268 include mutations that advantageously act to increase conversion efficiency in conversion from the compound (VII-a) to the compound (VIII-a).

Example 6

Preparation of Second-Generation Mutant Gene

In order to obtain mutant pSYN2-39cod having a higher conversion ratio, mutations of pEP77, pEP129, pEP139, and pEP268 were combined.

That is, pEP77 was digested with SalI and BamHI, so as to obtain a DNA fragment with a size of approximately 1.2 kb. This fragment was ligated to an *Escherichia coli* vector pHSG299 (manufactured by Takara Bio Inc.) that had also been digested with SalI and BamHI. Thereafter, *Escherichia coli* DH5α was transformed with the aforementioned vector, so as to produce recombinant DNA.

By the same procedures as described above, an approximately 1.2-kb SalI-BamHI-digested DNA fragment of each of pEP129, pEP139 and pEP268 was inserted into the SalI-BamHI site of pHSG299, so as to produce p129, p139 and p268.

An approximately 3.7-kb DNA fragment obtained by digesting p268 with EcoRV and BamHI was ligated to an approximately 0.2-kb DNA fragment obtained by digesting p139 with EcoRV and BamHI to produce recombinant DNA. Thereafter, *Escherichia coli* DH5α was transformed with the recombinant DNA, so as to produce p268a wherein an approximately 0.2-kb EcoRV-BamHI region on p268 was substituted with a p139-derived EcoRV-BamHI region.

By the same procedures as described above, an approximately 0.05-kb NcoI-HpaI region on p268a was substituted with a p139-derived approximately 0.05-kb NcoI-HpaI region to produce p346, an approximately 0.5-kb BglII-EcoRV region on p268a was substituted with a p77-derived approximately 0.5-kb BglII-EcoRV region to produce p509, an approximately 0.5-kb BglII-EcoRV region on p268a was substituted with a p139-derived approximately 0.5-kb BglII-EcoRV region to produce p709, and an approximately 1.4-kb Cfr10I-Cfr10I region (wherein either one exists on the vector side) on p268a was substituted with a p129-derived approximately 1.4-kb Cfr10I-Cfr10I region to produce p849.

Each of the thus obtained p346, p509, p709 and p849 was digested with SalI and BamHI, so as to obtain an approximately 1.2-kb SalI-BamHI DNA fragment. The thus obtained DNA fragment was ligated to pRI109 that had been digested with SalI and BamHI, so as to produce a recombinant DNA. Thereafter, *Escherichia coli* DH5α was transformed with the recombinant DNA, so as to produce pES346, pES509, pES709 and pES849.

Each of the aforementioned plasmids was introduced into a *C. ammoniagenes* ATCC21264 strain by the electroporation method, so as to obtain transformant strains. Each transformant strain was cultured by the method described in Example 2, and the activity of each strain of converting the compound (VII-a) to the compound (VIII-a) was measured (Table 3).

As shown in Table 3, all the strains exhibited conversion ratios higher than the transformant strain having the first-generation mutant gene. Thus, it became clear that conversion efficiency can be further increased by the combination of mutations.

Example 7

Preparation of Third-Generation Mutant Gene

The results of Example 3 suggested that the conversion efficiency of an enzyme catalyzing conversion from the compound (VII-a) to the compound (VIII-a), which is encoded by an approximately 1.2-kb SalI-BamHI fragment of pSYN2-39cod, be increased by substituting the serine residue at position 83 of the aforementioned enzyme with asparagine. Thus, the aforementioned substitution mutation was further introduced into the plasmid produced in Example 6.

Using pES346 as a template, and also using DNAs having the nucleotide sequences as shown in SEQ ID NOS: 43 and 44 as primers, PCR was carried out. As a PCR reaction, incubation was performed at 96° C. for 1 minute, and thereafter, a cycle consisting of 96° C.—1 minute, 58° C.—1 minute and 72° C.—1 minute was repeated 25 times. Thereafter, incubation was performed at 72° C. for 10 minutes.

An amplified DNA fragment with a size of approximately 330 by obtained by the aforementioned PCR was digested with SalI and HpaI, and it was then substituted with the corresponding SalI and HpaI portion of pES346, so as to produce pES78-1. Such pES78-1 was identical to pES346 with the exception that the serine residue at position 83 of an enzyme catalyzing conversion from the compound (VII-a) to the compound (VIII-a) was substituted with asparagine.

Likewise, pES849-1 was produced from pES849. In pES849-1, the serine residue at position 83 of an enzyme catalyzing conversion from the compound (VII-a) to the compound (VIII-a) was substituted with asparagine.

Moreover, an approximately 0.3-kb SalI-HpaI region of pES503 was substituted with an approximately 0.3-kb SalI-HpaI region derived from pES78-1, so as to produce pES503-1.

Each of pES78-1, pES849-1 and pES503-1 was introduced into a C. ammoniagenes ATCC21264 strain by the electroporation method, so as to obtain transformant strains. Each transformant strain was cultured by the method described in Example 2, and the activity of each strain of converting the compound (VII-a) to the compound (VIII-a) was measured. The results are shown in the above Table 3.

As shown in Table 3, in the enzymes wherein serine at position 83 was substituted with asparagine and in the enzyme comprising the pES78-1 mutation and the pES849-1 mutation in combination, the conversion efficiency of converting the compound (VII-a) to the compound (VIII-a) was increased.

The aforementioned results demonstrated that modification of the yjiB gene enables the improvement of conversion speed and conversion efficiency in conversion from the compound (VII-a) to the compound (VIII-a), and that such mutations bringing on a change in characteristics have additive effects. Therefore, it can be anticipated that enzymes comprising any given combination of the aforementioned mutations will also be excellent in term of conversion speed and/or conversion efficiency.

INDUSTRIAL APPLICABILITY

Using the protein of the invention of the present application, a compound that inhibits HMG-CoA reductase and has an action to decrease serum cholesterol can be produced in an industrially advantageous manner.

FREE TEXT OF THE SEQUENCE LISTING

SEQ ID NO:1 Explanation of Artificial sequence: synthesized DNA
SEQ ID NO:2 Explanation of Artificial sequence: synthesized DNA
SEQ ID NO:3 Explanation of Artificial sequence: synthesized DNA
SEQ ID NO:5 Explanation of Artificial sequence: synthesized DNA
SEQ ID NO:6 Explanation of Artificial sequence: synthesized DNA
SEQ ID NO:7 Explanation of Artificial sequence: synthesized DNA
SEQ ID NO:8 Explanation of Artificial sequence: synthesized DNA
SEQ ID NO:9 Explanation of Artificial sequence: synthesized DNA
SEQ ID NO:10 Explanation of Artificial sequence: synthesized DNA
SEQ ID NO:11 Explanation of Artificial sequence: synthesized DNA
SEQ ID NO:12 Explanation of Artificial sequence: synthesized DNA
SEQ ID NO:13 Explanation of Artificial sequence: synthesized DNA
SEQ ID NO:14 Explanation of Artificial sequence: synthesized DNA
SEQ ID NO:15 Explanation of Artificial sequence: synthesized DNA
SEQ ID NO:16 Explanation of Artificial sequence: synthesized DNA
SEQ ID NO:17 Explanation of Artificial sequence: synthesized DNA
SEQ ID NO:18 Explanation of Artificial sequence: synthesized DNA
SEQ ID NO:19 Explanation of Artificial sequence: synthesized DNA
SEQ ID NO:20 Explanation of Artificial sequence: synthesized DNA
SEQ ID NO:21 Explanation of Artificial sequence: synthesized DNA
SEQ ID NO:22 Explanation of Artificial sequence: synthesized DNA
SEQ ID NO:23 Explanation of Artificial sequence: synthesized DNA
SEQ ID NO:24 Explanation of Artificial sequence: synthesized DNA
SEQ ID NO:25 Explanation of Artificial sequence: synthesized DNA
SEQ ID NO:26 Explanation of Artificial sequence: synthesized DNA
SEQ ID NO:27 Explanation of Artificial sequence: synthesized DNA
SEQ ID NO:28 Explanation of Artificial sequence: synthesized DNA
SEQ ID NO:29 Explanation of Artificial sequence: synthesized DNA
SEQ ID NO:30 Explanation of Artificial sequence: synthesized DNA
SEQ ID NO:31 Explanation of Artificial sequence: synthesized DNA
SEQ ID NO:32 Explanation of Artificial sequence: synthesized DNA
SEQ ID NO:33 Explanation of Artificial sequence: synthesized DNA
SEQ ID NO:34 Explanation of Artificial sequence: synthesized DNA
SEQ ID NO:35 Explanation of Artificial sequence: synthesized DNA
SEQ ID NO:36 Explanation of Artificial sequence: synthesized DNA
SEQ ID NO:37 Explanation of Artificial sequence: synthesized DNA
SEQ ID NO:38 Explanation of Artificial sequence: synthesized DNA
SEQ ID NO:39 Explanation of Artificial sequence: synthesized DNA
SEQ ID NO:40 Explanation of Artificial sequence: synthesized DNA
SEQ ID NO:41 Explanation of Artificial sequence: synthesized DNA
SEQ ID NO:42 Explanation of Artificial sequence: synthesized DNA
SEQ ID NO:43 Explanation of Artificial sequence: synthesized DNA
SEQ ID NO:44 Explanation of Artificial sequence: synthesized DNA

The invention claimed is:

1. A process for producing a compound of Formula (XV):

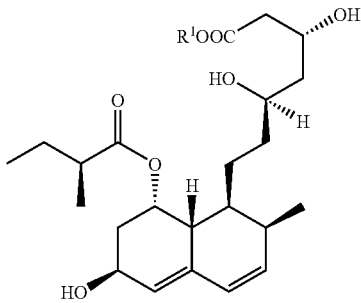
Formula(XV)

(wherein R¹ represents a hydrogen atom, a substituted or unsubstituted alkyl, or an alkali metal),
or a compound of Formula (XVI):

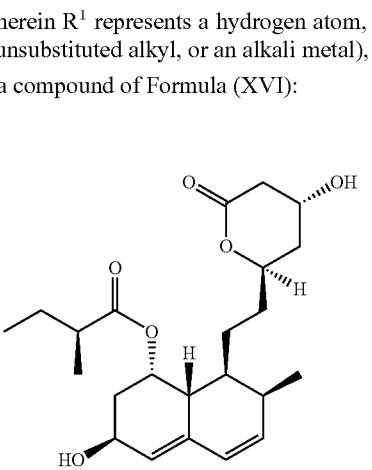
Formula(XVI)

which comprises: allowing a protein comprising the amino acid sequence as shown in SEQ ID NO:3, with the proviso that the proteins comprising the amino acid sequences as shown in SEQ ID NO: 4, 5, or 6 are excluded, to come into contact with a compound of Formula (XIII):

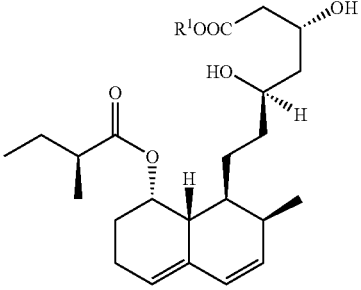
Formula(XIII)

(wherein R¹ represents a hydrogen atom, a substituted or unsubstituted alkyl, or an alkali metal), or a compound of Formula (XIV):

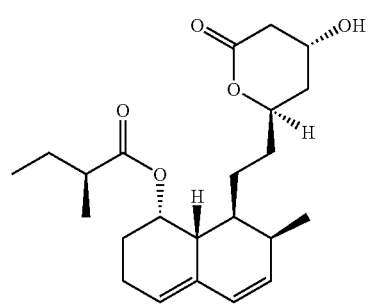
Formula(XIV)

so as to form the compound of Formula (XV) or Formula (XVI).

2. A process for producing a compound of Formula (XV):

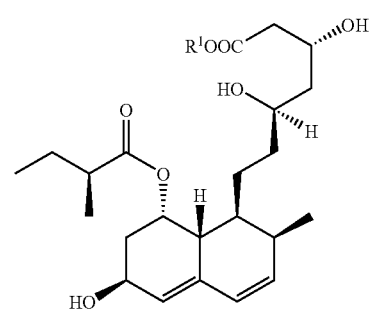
Formula(XV)

(wherein R¹ represents a hydrogen atom, a substituted or unsubstituted alkyl, or an alkali metal), or a compound of Formula (XVI):

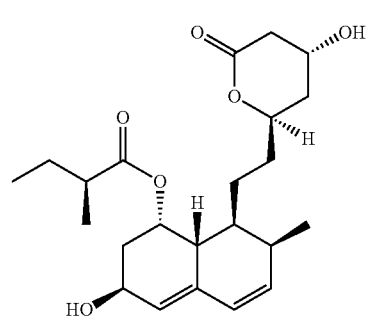
Formula(XVI)

which comprises: allowing a culture of a transformant having DNA encoding a protein comprising the amino acid sequence as shown in SEQ ID NO:3, with the proviso that DNA encoding the proteins comprising the amino acid sequences as shown in SEQ ID NO: 4, 5, or 6 are excluded, to come into contact with a compound of Formula (XIII):

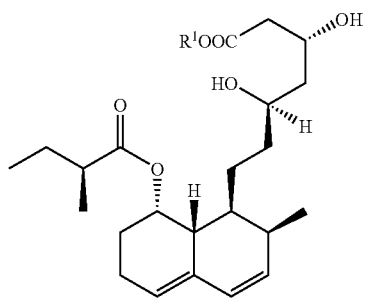
Formula (XIII)
(wherein R¹ represents a hydrogen atom, a substituted or unsubstituted alkyl, or an alkali metal), or a compound of Formula (XIV):
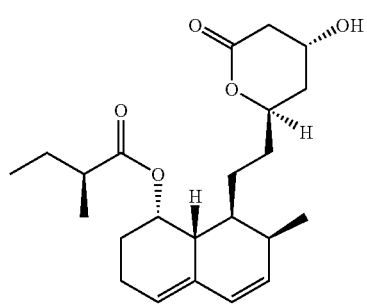
Formula (XIV)
in an aqueous medium, forming and accumulating the compound of Formula (XV) or Formula (XVI) in the aqueous medium, and recovering the compound of Formula (XV) or Formula (XVI) from the aqueous medium.
* * * * *

SEQUENCE LISTING

<160> NUMBER OF SEQ ID NOS: 46

<210> SEQ ID NO 1
<211> LENGTH: 396
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Ala, Arg, Asn, Asp, Cys, Glu, Gln, Gly, His,
      Ile, Leu, Lys, Met, Phe, Pro, Ser, Thr, Trp, Tyr or Val
<220> FEATURE:
<221> NAME/KEY: MOD_RES
<222> LOCATION: (14)..(14)
<223> OTHER INFORMATION: Ala, Arg, Asn, Asp, Cys, Glu, Gln, Gly, His,
      Ile, Leu, Lys, Met, Phe, Pro, Ser, Thr, Trp, Tyr or Val
<220> FEATURE:
<221> NAME/KEY: MOD_RES
<222> LOCATION: (16)..(18)
<223> OTHER INFORMATION: Ala, Arg, Asn, Asp, Cys, Glu, Gln, Gly, His,
      Ile, Leu, Lys, Met, Phe, Pro, Ser, Thr, Trp, Tyr or Val
<220> FEATURE:
<221> NAME/KEY: MOD_RES
<222> LOCATION: (35)..(35)
<223> OTHER INFORMATION: Ala, Arg, Asn, Asp, Cys, Glu, Gln, Gly, His,
      Ile, Leu, Lys, Met, Phe, Pro, Ser, Thr, Trp, Tyr or Val
<220> FEATURE:
<221> NAME/KEY: MOD_RES
<222> LOCATION: (83)..(83)
<223> OTHER INFORMATION: Ala, Arg, Asn, Asp, Cys, Glu, Gln, Gly, His,
      Ile, Leu, Lys, Met, Phe, Pro, Ser, Thr, Trp, Tyr or Val
<220> FEATURE:
<221> NAME/KEY: MOD_RES
<222> LOCATION: (104)..(104)
<223> OTHER INFORMATION: Ala, Arg, Asn, Asp, Cys, Glu, Gln, Gly, His,
      Ile, Leu, Lys, Met, Phe, Pro, Ser, Thr, Trp, Tyr or Val
<220> FEATURE:
<221> NAME/KEY: MOD_RES
<222> LOCATION: (123)..(123)
<223> OTHER INFORMATION: Ala, Arg, Asn, Asp, Cys, Glu, Gln, Gly, His,
      Ile, Leu, Lys, Met, Phe, Pro, Ser, Thr, Trp, Tyr or Val
<220> FEATURE:
<221> NAME/KEY: MOD_RES
<222> LOCATION: (132)..(132)
<223> OTHER INFORMATION: Ala, Arg, Asn, Asp, Cys, Glu, Gln, Gly, His,
      Ile, Leu, Lys, Met, Phe, Pro, Ser, Thr, Trp, Tyr or Val
<220> FEATURE:
<221> NAME/KEY: MOD_RES
<222> LOCATION: (135)..(135)
<223> OTHER INFORMATION: Ala, Arg, Asn, Asp, Cys, Glu, Gln, Gly, His,
      Ile, Leu, Lys, Met, Phe, Pro, Ser, Thr, Trp, Tyr or Val
<220> FEATURE:
<221> NAME/KEY: MOD_RES
<222> LOCATION: (143)..(143)
<223> OTHER INFORMATION: Ala, Arg, Asn, Asp, Cys, Glu, Gln, Gly, His,
      Ile, Leu, Lys, Met, Phe, Pro, Ser, Thr, Trp, Tyr or Val
<220> FEATURE:
<221> NAME/KEY: MOD_RES
<222> LOCATION: (154)..(154)
<223> OTHER INFORMATION: Ala, Arg, Asn, Asp, Cys, Glu, Gln, Gly, His,
      Ile, Leu, Lys, Met, Phe, Pro, Ser, Thr, Trp, Tyr or Val
<220> FEATURE:
<221> NAME/KEY: MOD_RES
<222> LOCATION: (187)..(187)
<223> OTHER INFORMATION: Ala, Arg, Asn, Asp, Cys, Glu, Gln, Gly, His,
      Ile, Leu, Lys, Met, Phe, Pro, Ser, Thr, Trp, Tyr or Val
<220> FEATURE:
<221> NAME/KEY: MOD_RES
<222> LOCATION: (232)..(232)
<223> OTHER INFORMATION: Ala, Arg, Asn, Asp, Cys, Glu, Gln, Gly, His,
      Ile, Leu, Lys, Met, Phe, Pro, Ser, Thr, Trp, Tyr or Val
<220> FEATURE:
<221> NAME/KEY: MOD_RES
<222> LOCATION: (253)..(253)

```
<223> OTHER INFORMATION: Ala, Arg, Asn, Asp, Cys, Glu, Gln, Gly, His,
      Ile, Leu, Lys, Met, Phe, Pro, Ser, Thr, Trp, Tyr or Val
<220> FEATURE:
<221> NAME/KEY: MOD_RES
<222> LOCATION: (284)..(284)
<223> OTHER INFORMATION: Ala, Arg, Asn, Asp, Cys, Glu, Gln, Gly, His,
      Ile, Leu, Lys, Met, Phe, Pro, Ser, Thr, Trp, Tyr or Val
<220> FEATURE:
<221> NAME/KEY: MOD_RES
<222> LOCATION: (306)..(306)
<223> OTHER INFORMATION: Ala, Arg, Asn, Asp, Cys, Glu, Gln, Gly, His,
      Ile, Leu, Lys, Met, Phe, Pro, Ser, Thr, Trp, Tyr or Val
<220> FEATURE:
<221> NAME/KEY: MOD_RES
<222> LOCATION: (309)..(309)
<223> OTHER INFORMATION: Ala, Arg, Asn, Asp, Cys, Glu, Gln, Gly, His,
      Ile, Leu, Lys, Met, Phe, Pro, Ser, Thr, Trp, Tyr or Val
<220> FEATURE:
<221> NAME/KEY: MOD_RES
<222> LOCATION: (343)..(343)
<223> OTHER INFORMATION: Ala, Arg, Asn, Asp, Cys, Glu, Gln, Gly, His,
      Ile, Leu, Lys, Met, Phe, Pro, Ser, Thr, Trp, Tyr or Val
<220> FEATURE:
<221> NAME/KEY: MOD_RES
<222> LOCATION: (357)..(357)
<223> OTHER INFORMATION: Ala, Arg, Asn, Asp, Cys, Glu, Gln, Gly, His,
      Ile, Leu, Lys, Met, Phe, Pro, Ser, Thr, Trp, Tyr or Val

<400> SEQUENCE: 1

Met Asn Val Leu Asn Arg Arg Gln Ala Leu Xaa Arg Ala Xaa Leu Xaa
1               5                   10                  15

Xaa Xaa Asn Lys Gln Asp Ala Tyr His Pro Phe Pro Trp Tyr Glu Ser
            20                  25                  30

Met Arg Xaa Asp Ala Pro Val Ser Phe Asp Glu Glu Asn Gln Val Trp
        35                  40                  45

Ser Val Phe Leu Tyr Asp Asp Val Lys Lys Val Val Gly Asp Lys Glu
    50                  55                  60

Leu Phe Ser Ser Cys Met Pro Gln Gln Thr Ser Ser Ile Gly Asn Ser
65                  70                  75                  80

Ile Ile Xaa Met Asp Pro Pro Lys His Thr Lys Ile Arg Ser Val Val
                85                  90                  95

Asn Lys Ala Phe Thr Pro Arg Xaa Met Lys Gln Trp Glu Pro Arg Ile
            100                 105                 110

Gln Glu Ile Thr Asp Glu Leu Ile Gln Lys Xaa Gln Gly Arg Ser Glu
        115                 120                 125

Phe Asp Leu Xaa His Asp Xaa Ser Tyr Pro Leu Pro Val Ile Xaa Ile
    130                 135                 140

Ser Glu Leu Leu Gly Val Pro Ser Ala Xaa Met Glu Gln Phe Lys Ala
145                 150                 155                 160

Trp Ser Asp Leu Leu Val Ser Thr Pro Lys Asp Lys Ser Glu Glu Ala
                165                 170                 175

Glu Lys Ala Phe Leu Glu Glu Arg Asp Lys Xaa Glu Glu Leu Ala
            180                 185                 190

Ala Phe Phe Ala Gly Ile Ile Glu Glu Lys Arg Asn Lys Pro Glu Gln
    195                 200                 205

Asp Ile Ile Ser Ile Leu Val Glu Ala Glu Thr Gly Glu Lys Leu
210                 215                 220

Ser Gly Glu Glu Leu Ile Pro Xaa Cys Thr Leu Leu Leu Val Ala Gly
225                 230                 235                 240

Asn Glu Thr Thr Thr Asn Leu Ile Ser Asn Ala Met Xaa Ser Ile Leu
                245                 250                 255

Glu Thr Pro Gly Val Tyr Glu Glu Leu Arg Ser His Pro Glu Leu Met
            260                 265                 270
```

```
Pro Gln Ala Val Glu Glu Ala Leu Arg Phe Arg Xaa Pro Ala Pro Val
        275                 280                 285

Leu Arg Arg Ile Ala Lys Arg Asp Thr Glu Ile Gly Gly His Leu Ile
    290                 295                 300

Lys Xaa Gly Asp Xaa Val Leu Ala Phe Val Ala Ser Ala Asn Arg Asp
305                 310                 315                 320

Glu Ala Lys Phe Asp Arg Pro His Met Phe Asp Ile Arg Arg His Pro
                325                 330                 335

Asn Pro His Ile Ala Phe Xaa His Gly Ile His Phe Cys Leu Gly Ala
                340                 345                 350

Pro Leu Ala Arg Xaa Glu Ala Asn Ile Ala Leu Thr Ser Leu Ile Ser
                355                 360                 365

Ala Phe Pro His Met Glu Cys Val Ser Ile Thr Pro Ile Glu Asn Ser
        370                 375                 380

Val Ile Tyr Gly Leu Lys Ser Phe Arg Val Lys Met
385                 390                 395

<210> SEQ ID NO 2
<211> LENGTH: 396
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Gln or Pro
<220> FEATURE:
<221> NAME/KEY: MOD_RES
<222> LOCATION: (14)..(14)
<223> OTHER INFORMATION: Leu or Pro
<220> FEATURE:
<221> NAME/KEY: MOD_RES
<222> LOCATION: (16)..(16)
<223> OTHER INFORMATION: Asn, Ala, Val, Ile or Leu
<220> FEATURE:
<221> NAME/KEY: MOD_RES
<222> LOCATION: (17)..(17)
<223> OTHER INFORMATION: Gly, Ala, Val, Ile or Leu
<220> FEATURE:
<221> NAME/KEY: MOD_RES
<222> LOCATION: (18)..(18)
<223> OTHER INFORMATION: Lys, Arg or His
<220> FEATURE:
<221> NAME/KEY: MOD_RES
<222> LOCATION: (35)..(35)
<223> OTHER INFORMATION: Lys, Met, Ala, Ser, Gly or Thr
<220> FEATURE:
<221> NAME/KEY: MOD_RES
<222> LOCATION: (83)..(83)
<223> OTHER INFORMATION: Asn, Ser, Thr or Ala
<220> FEATURE:
<221> NAME/KEY: MOD_RES
<222> LOCATION: (104)..(104)
<223> OTHER INFORMATION: Val, Ala, Met, Gly, Thr or Ser
<220> FEATURE:
<221> NAME/KEY: MOD_RES
<222> LOCATION: (123)..(123)
<223> OTHER INFORMATION: Phe, Ala, Val, Leu or Ile
<220> FEATURE:
<221> NAME/KEY: MOD_RES
<222> LOCATION: (132)..(132)
<223> OTHER INFORMATION: Val, Met, Gly, Ala, Thr or Ser
<220> FEATURE:
<221> NAME/KEY: MOD_RES
<222> LOCATION: (135)..(135)
<223> OTHER INFORMATION: Phe or Tyr
<220> FEATURE:
<221> NAME/KEY: MOD_RES
<222> LOCATION: (143)..(143)
```

```
<223> OTHER INFORMATION: Val, Met, Gly, Ala, Thr or Ser
<220> FEATURE:
<221> NAME/KEY: MOD_RES
<222> LOCATION: (154)..(154)
<223> OTHER INFORMATION: His, Lys or Arg
<220> FEATURE:
<221> NAME/KEY: MOD_RES
<222> LOCATION: (187)..(187)
<223> OTHER INFORMATION: Cys, Tyr, Phe, Trp, Ser or Thr
<220> FEATURE:
<221> NAME/KEY: MOD_RES
<222> LOCATION: (232)..(232)
<223> OTHER INFORMATION: Phe, Ala, Val, Leu or Ile
<220> FEATURE:
<221> NAME/KEY: MOD_RES
<222> LOCATION: (253)..(253)
<223> OTHER INFORMATION: Tyr, Phe or Trp
<220> FEATURE:
<221> NAME/KEY: MOD_RES
<222> LOCATION: (284)..(284)
<223> OTHER INFORMATION: Ala, Thr or Ser
<220> FEATURE:
<221> NAME/KEY: MOD_RES
<222> LOCATION: (306)..(306)
<223> OTHER INFORMATION: Glu, Met, Gly, Ala, Thr or Ser
<220> FEATURE:
<221> NAME/KEY: MOD_RES
<222> LOCATION: (309)..(309)
<223> OTHER INFORMATION: Met, Thr, Ala, Val, Leu or Ile
<220> FEATURE:
<221> NAME/KEY: MOD_RES
<222> LOCATION: (343)..(343)
<223> OTHER INFORMATION: Gly, Ala, Val, Leu or Ile
<220> FEATURE:
<221> NAME/KEY: MOD_RES
<222> LOCATION: (357)..(357)
<223> OTHER INFORMATION: Leu or Pro

<400> SEQUENCE: 2

Met Asn Val Leu Asn Arg Arg Gln Ala Leu Xaa Arg Ala Xaa Leu Xaa
1               5                   10                  15

Xaa Xaa Asn Lys Gln Asp Ala Tyr His Pro Phe Pro Trp Tyr Glu Ser
                20                  25                  30

Met Arg Xaa Asp Ala Pro Val Ser Phe Asp Glu Glu Asn Gln Val Trp
            35                  40                  45

Ser Val Phe Leu Tyr Asp Asp Val Lys Lys Val Val Gly Asp Lys Glu
50                  55                  60

Leu Phe Ser Ser Cys Met Pro Gln Gln Thr Ser Ser Ile Gly Asn Ser
65                  70                  75                  80

Ile Ile Xaa Met Asp Pro Pro Lys His Thr Lys Ile Arg Ser Val Val
                85                  90                  95

Asn Lys Ala Phe Thr Pro Arg Xaa Met Lys Gln Trp Glu Pro Arg Ile
                100                 105                 110

Gln Glu Ile Thr Asp Glu Leu Ile Gln Lys Xaa Gln Gly Arg Ser Glu
            115                 120                 125

Phe Asp Leu Xaa His Asp Xaa Ser Tyr Pro Leu Pro Val Ile Xaa Ile
130                 135                 140

Ser Glu Leu Leu Gly Val Pro Ser Ala Xaa Met Glu Gln Phe Lys Ala
145                 150                 155                 160

Trp Ser Asp Leu Leu Val Ser Thr Pro Lys Asp Lys Ser Glu Glu Ala
                165                 170                 175

Glu Lys Ala Phe Leu Glu Glu Arg Asp Lys Xaa Glu Glu Leu Ala
            180                 185                 190

Ala Phe Phe Ala Gly Ile Ile Glu Glu Lys Arg Asn Lys Pro Glu Gln
            195                 200                 205

Asp Ile Ile Ser Ile Leu Val Glu Ala Glu Glu Thr Gly Glu Lys Leu
```

```
                    210                 215                 220
Ser Gly Glu Glu Leu Ile Pro Xaa Cys Thr Leu Leu Val Ala Gly
225                 230                 235                 240

Asn Glu Thr Thr Thr Asn Leu Ile Ser Asn Ala Met Xaa Ser Ile Leu
                245                 250                 255

Glu Thr Pro Gly Val Tyr Glu Leu Arg Ser His Pro Glu Leu Met
                260                 265                 270

Pro Gln Ala Val Glu Glu Ala Leu Arg Phe Arg Xaa Pro Ala Pro Val
            275                 280                 285

Leu Arg Arg Ile Ala Lys Arg Asp Thr Glu Ile Gly Gly His Leu Ile
        290                 295                 300

Lys Xaa Gly Asp Xaa Val Leu Ala Phe Val Ala Ser Ala Asn Arg Asp
305                 310                 315                 320

Glu Ala Lys Phe Asp Arg Pro His Met Phe Asp Ile Arg Arg His Pro
                325                 330                 335

Asn Pro His Ile Ala Phe Xaa His Gly Ile His Phe Cys Leu Gly Ala
                340                 345                 350

Pro Leu Ala Arg Xaa Glu Ala Asn Ile Ala Leu Thr Ser Leu Ile Ser
            355                 360                 365

Ala Phe Pro His Met Glu Cys Val Ser Ile Thr Pro Ile Glu Asn Ser
        370                 375                 380

Val Ile Tyr Gly Leu Lys Ser Phe Arg Val Lys Met
385                 390                 395

<210> SEQ ID NO 3
<211> LENGTH: 396
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Gln or Pro
<220> FEATURE:
<221> NAME/KEY: MOD_RES
<222> LOCATION: (14)..(14)
<223> OTHER INFORMATION: Leu or Pro
<220> FEATURE:
<221> NAME/KEY: MOD_RES
<222> LOCATION: (16)..(16)
<223> OTHER INFORMATION: Asn or Ile
<220> FEATURE:
<221> NAME/KEY: MOD_RES
<222> LOCATION: (17)..(17)
<223> OTHER INFORMATION: Gly or Val
<220> FEATURE:
<221> NAME/KEY: MOD_RES
<222> LOCATION: (18)..(18)
<223> OTHER INFORMATION: Lys or Arg
<220> FEATURE:
<221> NAME/KEY: MOD_RES
<222> LOCATION: (35)..(35)
<223> OTHER INFORMATION: Lys or Met
<220> FEATURE:
<221> NAME/KEY: MOD_RES
<222> LOCATION: (83)..(83)
<223> OTHER INFORMATION: Asn or Ser
<220> FEATURE:
<221> NAME/KEY: MOD_RES
<222> LOCATION: (104)..(104)
<223> OTHER INFORMATION: Val or Ala
<220> FEATURE:
<221> NAME/KEY: MOD_RES
<222> LOCATION: (123)..(123)
<223> OTHER INFORMATION: Phe or Leu
<220> FEATURE:
```

```
<221> NAME/KEY: MOD_RES
<222> LOCATION: (132)..(132)
<223> OTHER INFORMATION: Val or Gly
<220> FEATURE:
<221> NAME/KEY: MOD_RES
<222> LOCATION: (135)..(135)
<223> OTHER INFORMATION: Phe or Tyr
<220> FEATURE:
<221> NAME/KEY: MOD_RES
<222> LOCATION: (143)..(143)
<223> OTHER INFORMATION: Val or Gly
<220> FEATURE:
<221> NAME/KEY: MOD_RES
<222> LOCATION: (154)..(154)
<223> OTHER INFORMATION: His or Arg
<220> FEATURE:
<221> NAME/KEY: MOD_RES
<222> LOCATION: (187)..(187)
<223> OTHER INFORMATION: Cys or Tyr
<220> FEATURE:
<221> NAME/KEY: MOD_RES
<222> LOCATION: (232)..(232)
<223> OTHER INFORMATION: Phe or Leu
<220> FEATURE:
<221> NAME/KEY: MOD_RES
<222> LOCATION: (253)..(253)
<223> OTHER INFORMATION: Tyr or Phe
<220> FEATURE:
<221> NAME/KEY: MOD_RES
<222> LOCATION: (284)..(284)
<223> OTHER INFORMATION: Ala or Thr
<220> FEATURE:
<221> NAME/KEY: MOD_RES
<222> LOCATION: (306)..(306)
<223> OTHER INFORMATION: Glu or Gly
<220> FEATURE:
<221> NAME/KEY: MOD_RES
<222> LOCATION: (309)..(309)
<223> OTHER INFORMATION: Met or Thr
<220> FEATURE:
<221> NAME/KEY: MOD_RES
<222> LOCATION: (343)..(343)
<223> OTHER INFORMATION: Gly or Ala
<220> FEATURE:
<221> NAME/KEY: MOD_RES
<222> LOCATION: (357)..(357)
<223> OTHER INFORMATION: Leu or Pro

<400> SEQUENCE: 3

Met Asn Val Leu Asn Arg Arg Gln Ala Leu Xaa Arg Ala Xaa Leu Xaa
1               5                   10                  15

Xaa Xaa Asn Lys Gln Asp Ala Tyr His Pro Phe Pro Trp Tyr Glu Ser
            20                  25                  30

Met Arg Xaa Asp Ala Pro Val Ser Phe Asp Glu Glu Asn Gln Val Trp
        35                  40                  45

Ser Val Phe Leu Tyr Asp Asp Val Lys Lys Val Val Gly Asp Lys Glu
    50                  55                  60

Leu Phe Ser Ser Cys Met Pro Gln Gln Thr Ser Ser Ile Gly Asn Ser
65                  70                  75                  80

Ile Ile Xaa Met Asp Pro Pro Lys His Thr Lys Ile Arg Ser Val Val
                85                  90                  95

Asn Lys Ala Phe Thr Pro Arg Xaa Met Lys Gln Trp Glu Pro Arg Ile
            100                 105                 110

Gln Glu Ile Thr Asp Glu Leu Ile Gln Lys Xaa Gln Gly Arg Ser Glu
        115                 120                 125

Phe Asp Leu Xaa His Asp Xaa Ser Tyr Pro Leu Pro Val Ile Xaa Ile
    130                 135                 140

Ser Glu Leu Leu Gly Val Pro Ser Ala Xaa Met Glu Gln Phe Lys Ala
145                 150                 155                 160
```

```
Trp Ser Asp Leu Leu Val Ser Thr Pro Lys Asp Lys Ser Glu Glu Ala
            165                 170                 175

Glu Lys Ala Phe Leu Glu Arg Asp Lys Xaa Glu Glu Glu Leu Ala
        180                 185                 190

Ala Phe Phe Ala Gly Ile Ile Glu Lys Arg Asn Lys Pro Glu Gln
        195                 200                 205

Asp Ile Ile Ser Ile Leu Val Glu Ala Glu Thr Gly Lys Leu
        210                 215                 220

Ser Gly Glu Glu Leu Ile Pro Xaa Cys Thr Leu Leu Val Ala Gly
225                 230                 235                 240

Asn Glu Thr Thr Thr Asn Leu Ile Ser Asn Ala Met Xaa Ser Ile Leu
                245                 250                 255

Glu Thr Pro Gly Val Tyr Glu Glu Leu Arg Ser His Pro Glu Leu Met
            260                 265                 270

Pro Gln Ala Val Glu Glu Ala Leu Arg Phe Arg Xaa Pro Ala Pro Val
        275                 280                 285

Leu Arg Arg Ile Ala Lys Arg Asp Thr Glu Ile Gly Gly His Leu Ile
    290                 295                 300

Lys Xaa Gly Asp Xaa Val Leu Ala Phe Val Ala Ser Ala Asn Arg Asp
305                 310                 315                 320

Glu Ala Lys Phe Asp Arg Pro His Met Phe Asp Ile Arg Arg His Pro
                325                 330                 335

Asn Pro His Ile Ala Phe Xaa His Gly Ile His Phe Cys Leu Gly Ala
            340                 345                 350

Pro Leu Ala Arg Xaa Glu Ala Asn Ile Ala Leu Thr Ser Leu Ile Ser
        355                 360                 365

Ala Phe Pro His Met Glu Cys Val Ser Ile Thr Pro Ile Glu Asn Ser
    370                 375                 380

Val Ile Tyr Gly Leu Lys Ser Phe Arg Val Lys Met
385                 390                 395

<210> SEQ ID NO 4
<211> LENGTH: 396
<212> TYPE: PRT
<213> ORGANISM: Bacillus subtilis

<400> SEQUENCE: 4

Met Asn Val Leu Asn Arg Arg Gln Ala Leu Gln Arg Ala Leu Leu Asn
1               5                   10                  15

Gly Lys Asn Lys Gln Asp Ala Tyr His Pro Phe Pro Trp Tyr Glu Ser
            20                  25                  30

Met Arg Lys Asp Ala Pro Val Ser Phe Asp Glu Glu Asn Gln Val Trp
        35                  40                  45

Ser Val Phe Leu Tyr Asp Asp Val Lys Lys Val Val Gly Asp Lys Glu
    50                  55                  60

Leu Phe Ser Ser Cys Met Pro Gln Gln Thr Ser Ser Ile Gly Asn Ser
65                  70                  75                  80

Ile Ile Asn Met Asp Pro Pro Lys His Thr Lys Ile Arg Ser Val Val
                85                  90                  95

Asn Lys Ala Phe Thr Pro Arg Val Met Lys Gln Trp Glu Pro Arg Ile
            100                 105                 110

Gln Glu Ile Thr Asp Glu Leu Ile Gln Lys Phe Gln Gly Arg Ser Glu
        115                 120                 125

Phe Asp Leu Val His Asp Phe Ser Tyr Pro Leu Pro Val Ile Val Ile
    130                 135                 140
```

```
Ser Glu Leu Leu Gly Val Pro Ser Ala His Met Glu Gln Phe Lys Ala
145                 150                 155                 160

Trp Ser Asp Leu Leu Val Ser Thr Pro Lys Asp Lys Ser Glu Glu Ala
            165                 170                 175

Glu Lys Ala Phe Leu Glu Glu Arg Asp Lys Cys Glu Glu Glu Leu Ala
        180                 185                 190

Ala Phe Phe Ala Gly Ile Ile Glu Glu Lys Arg Asn Lys Pro Glu Gln
    195                 200                 205

Asp Ile Ile Ser Ile Leu Val Glu Ala Glu Glu Thr Gly Glu Lys Leu
210                 215                 220

Ser Gly Glu Glu Leu Ile Pro Phe Cys Thr Leu Leu Val Ala Gly
225                 230                 235                 240

Asn Glu Thr Thr Thr Asn Leu Ile Ser Asn Ala Met Tyr Ser Ile Leu
            245                 250                 255

Glu Thr Pro Gly Val Tyr Glu Glu Leu Arg Ser His Pro Glu Leu Met
        260                 265                 270

Pro Gln Ala Val Glu Glu Ala Leu Arg Phe Arg Ala Pro Ala Pro Val
    275                 280                 285

Leu Arg Arg Ile Ala Lys Arg Asp Thr Glu Ile Gly Gly His Leu Ile
290                 295                 300

Lys Glu Gly Asp Met Val Leu Ala Phe Val Ala Ser Ala Asn Arg Asp
305                 310                 315                 320

Glu Ala Lys Phe Asp Arg Pro His Met Phe Asp Ile Arg Arg His Pro
            325                 330                 335

Asn Pro His Ile Ala Phe Gly His Gly Ile His Phe Cys Leu Gly Ala
        340                 345                 350

Pro Leu Ala Arg Leu Glu Ala Asn Ile Ala Leu Thr Ser Leu Ile Ser
    355                 360                 365

Ala Phe Pro His Met Glu Cys Val Ser Ile Thr Pro Ile Glu Asn Ser
370                 375                 380

Val Ile Tyr Gly Leu Lys Ser Phe Arg Val Lys Met
385                 390                 395

<210> SEQ ID NO 5
<211> LENGTH: 396
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Asn Val Leu Asn Arg Arg Gln Ala Leu Gln Arg Ala Leu Leu Asn
1               5                   10                  15

Gly Lys Asn Lys Gln Asp Ala Tyr His Pro Phe Pro Trp Tyr Glu Ser
            20                  25                  30

Met Arg Lys Asp Ala Pro Val Ser Phe Asp Glu Asn Gln Val Trp
        35                  40                  45

Ser Val Phe Leu Tyr Asp Asp Val Lys Val Val Gly Asp Lys Glu
    50                  55                  60

Leu Phe Ser Ser Cys Met Pro Gln Gln Thr Ser Ser Ile Gly Asn Ser
65                  70                  75                  80

Ile Ile Asn Met Asp Pro Pro Lys His Thr Lys Ile Arg Ser Val Val
                85                  90                  95

Asn Lys Ala Phe Thr Pro Arg Ala Met Lys Gln Trp Glu Pro Arg Ile
            100                 105                 110
```

-continued

```
Gln Glu Ile Thr Asp Glu Leu Ile Gln Lys Phe Gln Gly Arg Ser Glu
        115                 120                 125

Phe Asp Leu Val His Asp Phe Ser Tyr Pro Leu Pro Val Ile Val Ile
130                 135                 140

Ser Glu Leu Leu Gly Val Pro Ser Ala His Met Glu Gln Phe Lys Ala
145                 150                 155                 160

Trp Ser Asp Leu Leu Val Ser Thr Pro Lys Asp Lys Ser Glu Glu Ala
                165                 170                 175

Glu Lys Ala Phe Leu Glu Glu Arg Asp Lys Cys Glu Glu Leu Ala
            180                 185                 190

Ala Phe Phe Ala Gly Ile Glu Glu Lys Arg Asn Lys Pro Glu Gln
        195                 200                 205

Asp Ile Ile Ser Ile Leu Val Glu Ala Glu Thr Gly Glu Lys Leu
    210                 215                 220

Ser Gly Glu Glu Leu Ile Pro Leu Cys Thr Leu Leu Leu Val Ala Gly
225                 230                 235                 240

Asn Glu Thr Thr Thr Asn Leu Ile Ser Asn Ala Met Tyr Ser Ile Leu
                245                 250                 255

Glu Thr Pro Gly Val Tyr Glu Glu Leu Arg Ser His Pro Glu Leu Met
            260                 265                 270

Pro Gln Ala Val Glu Glu Ala Leu Arg Phe Arg Ala Pro Ala Pro Val
        275                 280                 285

Leu Arg Arg Ile Ala Lys Arg Asp Thr Glu Ile Gly Gly His Leu Ile
    290                 295                 300

Lys Glu Gly Asp Met Val Leu Ala Phe Val Ala Ser Ala Asn Arg Asp
305                 310                 315                 320

Glu Ala Lys Phe Asp Arg Pro His Met Phe Asp Ile Arg Arg His Pro
                325                 330                 335

Asn Pro His Ile Ala Phe Gly His Gly Ile His Phe Cys Leu Gly Ala
            340                 345                 350

Pro Leu Ala Arg Leu Glu Ala Asn Ile Ala Leu Thr Ser Leu Ile Ser
        355                 360                 365

Ala Phe Pro His Met Glu Cys Val Ser Ile Thr Pro Ile Glu Asn Ser
    370                 375                 380

Val Ile Tyr Gly Leu Lys Ser Phe Arg Val Lys Met
385                 390                 395

<210> SEQ ID NO 6
<211> LENGTH: 396
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Asn Val Leu Asn Arg Arg Gln Ala Leu Pro Arg Ala Leu Leu Asn
1               5                   10                  15

Gly Lys Asn Lys Gln Asp Ala Tyr His Pro Phe Pro Trp Tyr Glu Ser
            20                  25                  30

Met Arg Lys Asp Ala Pro Val Ser Phe Asp Glu Glu Asn Gln Val Trp
        35                  40                  45

Ser Val Phe Leu Tyr Asp Asp Val Lys Lys Val Val Gly Asp Lys Glu
    50                  55                  60

Leu Phe Ser Ser Cys Met Pro Gln Gln Thr Ser Ser Ile Gly Asn Ser
65                  70                  75                  80
```

```
Ile Ile Ser Met Asp Pro Pro Lys His Thr Lys Ile Arg Ser Val Val
            85                  90                  95

Asn Lys Ala Phe Thr Pro Arg Ala Met Lys Gln Trp Glu Pro Arg Ile
        100                 105                 110

Gln Glu Ile Thr Asp Glu Leu Ile Gln Lys Phe Gln Gly Arg Ser Glu
            115                 120                 125

Phe Asp Leu Val His Asp Tyr Ser Tyr Pro Leu Pro Val Ile Val Ile
        130                 135                 140

Ser Glu Leu Leu Gly Val Pro Ser Ala His Met Glu Gln Phe Lys Ala
145                 150                 155                 160

Trp Ser Asp Leu Leu Val Ser Thr Pro Lys Asp Lys Ser Glu Glu Ala
                165                 170                 175

Glu Lys Ala Phe Leu Glu Glu Arg Asp Lys Cys Glu Glu Leu Ala
        180                 185                 190

Ala Phe Phe Ala Gly Ile Ile Glu Glu Lys Arg Asn Lys Pro Glu Gln
        195                 200                 205

Asp Ile Ile Ser Ile Leu Val Glu Ala Glu Glu Thr Gly Glu Lys Leu
        210                 215                 220

Ser Gly Glu Glu Leu Ile Pro Leu Cys Thr Leu Leu Val Ala Gly
225                 230                 235                 240

Asn Glu Thr Thr Thr Asn Leu Ile Ser Asn Ala Met Phe Ser Ile Leu
                245                 250                 255

Glu Thr Pro Gly Val Tyr Glu Glu Leu Arg Ser His Pro Glu Leu Met
            260                 265                 270

Pro Gln Ala Val Glu Ala Leu Arg Phe Arg Ala Pro Ala Pro Val
        275                 280                 285

Leu Arg Arg Ile Ala Lys Arg Asp Thr Glu Ile Gly Gly His Leu Ile
        290                 295                 300

Lys Glu Gly Asp Thr Val Leu Ala Phe Val Ala Ser Ala Asn Arg Asp
305                 310                 315                 320

Glu Ala Lys Phe Asp Arg Pro His Met Phe Asp Ile Arg Arg His Pro
                325                 330                 335

Asn Pro His Ile Ala Phe Gly His Gly Ile His Phe Cys Leu Gly Ala
            340                 345                 350

Pro Leu Ala Arg Leu Glu Ala Asn Ile Ala Leu Thr Ser Leu Ile Ser
        355                 360                 365

Ala Phe Pro His Met Glu Cys Val Ser Ile Thr Pro Ile Glu Asn Ser
        370                 375                 380

Val Ile Tyr Gly Leu Lys Ser Phe Arg Val Lys Met
385                 390                 395

<210> SEQ ID NO 7
<211> LENGTH: 1188
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
atgaacgttc tgaaccgccg ccaggcactg cmgcgcgcac ygctcawcgk cargaacaag      60
caggatgcat accatccatt tccatggtac gaatccatgc gcawggatgc accagtttcc     120
tttgatgaag aaaaccaggt tggagcgtt tttctttacg atgatgtcaa gaaggttgtt     180
ggcgataagg agctgttttc ctcctgcatg ccacagcaga ccagctctat tggaaactcc     240
atcattarca tggacccacc aaagcatacc aagatccgtt ccgtcgttaa caaggcattt     300
```

-continued

```
actccgcgcg ytatgaagca gtgggaacca cgcattcagg aaatcaccga tgaactgatt      360
cagaagyttc agggccgcag tgagtttgac cttgktcacg attwttccta cccacttcca      420
gttattgkta tctctgagct gctgggagtt ccttccgcac rtatggaaca gtttaaggca      480
tggtctgatc ttctggtctc caccccaaag gataagtccg aagaagctga aaaggcattt      540
ctggaagaac gcgataagtr cgaggaagaa ctggcagcat tttttgcagg catcatcgaa      600
gaaaagcgca acaagccgga acaggatatt atttctattc tggttgaagc agaagaaacc      660
ggcgagaagc tgtccggtga agagctgatt ccgttktgca ccctgctgct ggttgcagga      720
aacgaaacca ctaccaacct gatttccaac gcaatgtwca gcatcctgga aaccccaggc      780
gtttacgagg aactgcgcag ccatcctgaa ctgatgcctc aggcagttga ggaagccctg      840
cgtttccgcr caccagcacc agttctgcgc cgcatcgcaa agcgcgatac cgagatcggc      900
ggccacctga ttaaggragg tgatayggtt ctggcatttg ttgcatccgc aaaccgtgat      960
gaagcaaagt ttgaccgccc acacatgttt gatatccgcc gccatccaaa cccacatatt     1020
gcatttgscc acggcatcca tttttgcctt ggcgcaccac ttgcacgtcy tgaagcaaac     1080
atcgcactga cctctctgat ttctgctttt cctcatatgg agtgcgtctc catcactcca     1140
attgaaaact ccgttatcta cggactgaag agcttccgtg ttaagatg                  1188
```

<210> SEQ ID NO 8
<211> LENGTH: 1188
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1188)

<400> SEQUENCE: 8

```
atg aac gtt ctg aac cgc cgc cag gca ctg cag cgc gca ctg ctc aac       48
Met Asn Val Leu Asn Arg Arg Gln Ala Leu Gln Arg Ala Leu Leu Asn
1               5                   10                  15 ggc aag aac aag cag gat gca tac cat cca ttt cca tgg tac gaa tcc       96
Gly Lys Asn Lys Gln Asp Ala Tyr His Pro Phe Pro Trp Tyr Glu Ser
            20                  25                  30 atg cgc aag gat gca cca gtt tcc ttt gat gaa gaa aac cag gtt tgg      144
Met Arg Lys Asp Ala Pro Val Ser Phe Asp Glu Glu Asn Gln Val Trp
        35                  40                  45 agc gtt ttt ctt tac gat gat gtc aag aag gtt gtt ggc gat aag gag      192
Ser Val Phe Leu Tyr Asp Asp Val Lys Lys Val Val Gly Asp Lys Glu
    50                  55                  60 ctg ttt tcc tcc tgc atg cca cag cag acc agc tct att gga aac tcc      240
Leu Phe Ser Ser Cys Met Pro Gln Gln Thr Ser Ser Ile Gly Asn Ser
65                  70                  75                  80 atc att aac atg gac cca cca aag cat acc aag atc cgt tcc gtc gtt      288
Ile Ile Asn Met Asp Pro Pro Lys His Thr Lys Ile Arg Ser Val Val
                85                  90                  95 aac aag gca ttt act ccg cgc gct atg aag cag tgg gaa cca cgc att      336
Asn Lys Ala Phe Thr Pro Arg Ala Met Lys Gln Trp Glu Pro Arg Ile
            100                 105                 110 cag gaa atc acc gat gaa ctg att cag aag ttt cag ggc cgc agt gag      384
Gln Glu Ile Thr Asp Glu Leu Ile Gln Lys Phe Gln Gly Arg Ser Glu
        115                 120                 125 ttt gac ctt gtt cac gat ttt tcc tac cca ctt cca gtt att gtt atc      432
Phe Asp Leu Val His Asp Phe Ser Tyr Pro Leu Pro Val Ile Val Ile
    130                 135                 140
```

```
tct gag ctg ctg gga gtt cct tcc gca cat atg gaa cag ttt aag gca    480
Ser Glu Leu Leu Gly Val Pro Ser Ala His Met Glu Gln Phe Lys Ala
145                 150                 155                 160 tgg tct gat ctt ctg gtc tcc acc cca aag gat aag tcc gaa gaa gct    528
Trp Ser Asp Leu Leu Val Ser Thr Pro Lys Asp Lys Ser Glu Glu Ala
                165                 170                 175 gaa aag gca ttt ctg gaa gaa cgc gat aag tgc gag gaa ctg gca        576
Glu Lys Ala Phe Leu Glu Glu Arg Asp Lys Cys Glu Glu Glu Leu Ala
            180                 185                 190 gca ttt ttt gca ggc atc atc gaa gaa aag cgc aac aag ccg gaa cag    624
Ala Phe Phe Ala Gly Ile Ile Glu Glu Lys Arg Asn Lys Pro Glu Gln
        195                 200                 205 gat att att tct att ctg gtt gaa gca gaa gaa acc ggc gag aag ctg    672
Asp Ile Ile Ser Ile Leu Val Glu Ala Glu Glu Thr Gly Glu Lys Leu
    210                 215                 220 tcc ggt gaa gag ctg att ccg ttg tgc acc ctg ctg ctg gtt gca gga    720
Ser Gly Glu Glu Leu Ile Pro Leu Cys Thr Leu Leu Leu Val Ala Gly
225                 230                 235                 240 aac gaa acc act acc aac ctg att tcc aac gca atg tac agc atc ctg    768
Asn Glu Thr Thr Thr Asn Leu Ile Ser Asn Ala Met Tyr Ser Ile Leu
                245                 250                 255 gaa acc cca ggc gtt tac gag gaa ctg cgc agc cat cct gaa ctg atg    816
Glu Thr Pro Gly Val Tyr Glu Glu Leu Arg Ser His Pro Glu Leu Met
            260                 265                 270 cct cag gca gtt gag gaa gcc ctg cgt ttc cgc gca cca gca cca gtt    864
Pro Gln Ala Val Glu Glu Ala Leu Arg Phe Arg Ala Pro Ala Pro Val
        275                 280                 285 ctg cgc cgc atc gca aag cgc gat acc gag atc ggc ggc cac ctg att    912
Leu Arg Arg Ile Ala Lys Arg Asp Thr Glu Ile Gly Gly His Leu Ile
    290                 295                 300 aag gaa ggt gat atg gtt ctg gca ttt gtt gca tcc gca aac cgt gat    960
Lys Glu Gly Asp Met Val Leu Ala Phe Val Ala Ser Ala Asn Arg Asp
305                 310                 315                 320 gaa gca aag ttt gac cgc cca cac atg ttt gat atc cgc cgc cat cca   1008
Glu Ala Lys Phe Asp Arg Pro His Met Phe Asp Ile Arg Arg His Pro
                325                 330                 335 aac cca cat att gca ttt ggc cac ggc atc cat ttt tgc ctt ggc gca   1056
Asn Pro His Ile Ala Phe Gly His Gly Ile His Phe Cys Leu Gly Ala
            340                 345                 350 cca ctt gca cgt ctt gaa gca aac atc gca ctg acc tct ctg att tct   1104
Pro Leu Ala Arg Leu Glu Ala Asn Ile Ala Leu Thr Ser Leu Ile Ser
        355                 360                 365 gct ttt cct cat atg gag tgc gtc tcc atc act cca att gaa aac tcc   1152
Ala Phe Pro His Met Glu Cys Val Ser Ile Thr Pro Ile Glu Asn Ser
    370                 375                 380 gtt atc tac gga ctg aag agc ttc cgt gtt aag atg                   1188
Val Ile Tyr Gly Leu Lys Ser Phe Arg Val Lys Met
385                 390                 395

<210> SEQ ID NO 9
<211> LENGTH: 1188
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1188)

<400> SEQUENCE: 9 atg aac gtt ctg aac cgc cgc cag gca ctg ccg cgc gca ctg ctc aac     48
```

```
            Met Asn Val Leu Asn Arg Arg Gln Ala Leu Pro Arg Ala Leu Leu Asn
            1               5                   10                  15 ggc aag aac aag cag gat gca tac cat cca ttt cca tgg tac gaa tcc        96
Gly Lys Asn Lys Gln Asp Ala Tyr His Pro Phe Pro Trp Tyr Glu Ser
                20                  25                  30 atg cgc aag gat gca cca gtt tcc ttt gat gaa gaa aac cag gtt tgg       144
Met Arg Lys Asp Ala Pro Val Ser Phe Asp Glu Glu Asn Gln Val Trp
        35                  40                  45 agc gtt ttt ctt tac gat gat gtc aag aag gtt gtt ggc gat aag gag       192
Ser Val Phe Leu Tyr Asp Asp Val Lys Lys Val Val Gly Asp Lys Glu
    50                  55                  60 ctg ttt tcc tcc tgc atg cca cag cag acc agc tct att gga aac tcc       240
Leu Phe Ser Ser Cys Met Pro Gln Gln Thr Ser Ser Ile Gly Asn Ser
65                  70                  75                  80 atc att agc atg gac cca cca aag cat acc aag atc cgt tcc gtc gtt       288
Ile Ile Ser Met Asp Pro Pro Lys His Thr Lys Ile Arg Ser Val Val
                85                  90                  95 aac aag gca ttt act ccg cgc gct atg aag cag tgg gaa cca cgc att       336
Asn Lys Ala Phe Thr Pro Arg Ala Met Lys Gln Trp Glu Pro Arg Ile
            100                 105                 110 cag gaa atc acc gat gaa ctg att cag aag ttt cag ggc cgc agt gag       384
Gln Glu Ile Thr Asp Glu Leu Ile Gln Lys Phe Gln Gly Arg Ser Glu
        115                 120                 125 ttt gac ctt gtt cac gat tat tcc tac cca ctt cca gtt att gtt atc       432
Phe Asp Leu Val His Asp Tyr Ser Tyr Pro Leu Pro Val Ile Val Ile
    130                 135                 140 tct gag ctg ctg gga gtt cct tcc gca cat atg gaa cag ttt aag gca       480
Ser Glu Leu Leu Gly Val Pro Ser Ala His Met Glu Gln Phe Lys Ala
145                 150                 155                 160 tgg tct gat ctt ctg gtc tcc acc cca aag gat aag tcc gaa gaa gct       528
Trp Ser Asp Leu Leu Val Ser Thr Pro Lys Asp Lys Ser Glu Glu Ala
                165                 170                 175 gaa aag gca ttt ctg gaa gaa cgc gat aag tgc gag gaa gaa ctg gca       576
Glu Lys Ala Phe Leu Glu Glu Arg Asp Lys Cys Glu Glu Glu Leu Ala
            180                 185                 190 gca ttt ttt gca ggc atc atc gaa gaa aag cgc aac aag ccg gaa cag       624
Ala Phe Phe Ala Gly Ile Ile Glu Glu Lys Arg Asn Lys Pro Glu Gln
        195                 200                 205 gat att att tct att ctg gtt gaa gca gaa gaa acc ggc gag aag ctg       672
Asp Ile Ile Ser Ile Leu Val Glu Ala Glu Glu Thr Gly Glu Lys Leu
    210                 215                 220 tcc ggt gaa gag ctg att ccg ttg tgc acc ctg ctg ctg gtt gca gga       720
Ser Gly Glu Glu Leu Ile Pro Leu Cys Thr Leu Leu Leu Val Ala Gly
225                 230                 235                 240 aac gaa acc act acc aac ctg att tcc aac gca atg ttc agc atc ctg       768
Asn Glu Thr Thr Thr Asn Leu Ile Ser Asn Ala Met Phe Ser Ile Leu
                245                 250                 255 gaa acc cca ggc gtt tac gag gaa ctg cgc agc cat cct gaa ctg atg       816
Glu Thr Pro Gly Val Tyr Glu Glu Leu Arg Ser His Pro Glu Leu Met
            260                 265                 270 cct cag gca gtt gag gaa gcc ctg cgt ttc cgc gca cca gca cca gtt       864
Pro Gln Ala Val Glu Glu Ala Leu Arg Phe Arg Ala Pro Ala Pro Val
        275                 280                 285 ctg cgc cgc atc gca aag cgc gat acc gag atc ggc ggc cac ctg att       912
Leu Arg Arg Ile Ala Lys Arg Asp Thr Glu Ile Gly Gly His Leu Ile
    290                 295                 300 aag gaa ggt gat acg gtt ctg gca ttt gtt gca tcc gca aac cgt gat       960
Lys Glu Gly Asp Thr Val Leu Ala Phe Val Ala Ser Ala Asn Arg Asp
305                 310                 315                 320 gaa gca aag ttt gac cgc cca cac atg ttt gat atc cgc cgc cat cca      1008
```

```
                                             -continued

Glu Ala Lys Phe Asp Arg Pro His Met Phe Asp Ile Arg Arg His Pro
                325                 330                 335 aac cca cat att gca ttt ggc cac ggc atc cat ttt tgc ctt ggc gca      1056
Asn Pro His Ile Ala Phe Gly His Gly Ile His Phe Cys Leu Gly Ala
            340                 345                 350 cca ctt gca cgt ctt gaa gca aac atc gca ctg acc tct ctg att tct      1104
Pro Leu Ala Arg Leu Glu Ala Asn Ile Ala Leu Thr Ser Leu Ile Ser
        355                 360                 365 gct ttt cct cat atg gag tgc gtc tcc atc act cca att gaa aac tcc      1152
Ala Phe Pro His Met Glu Cys Val Ser Ile Thr Pro Ile Glu Asn Ser
    370                 375                 380 gtt atc tac gga ctg aag agc ttc cgt gtt aag atg                      1188
Val Ile Tyr Gly Leu Lys Ser Phe Arg Val Lys Met
385                 390                 395

<210> SEQ ID NO 10
<211> LENGTH: 138
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
acgcgtcgac taatatgaac gttctgaacc gccgccaggc actgccacgc gcactgctca    60
acggcaagaa caagcaggat gcataccatc catttccatg gtacgaatcc atgcgcaagg    120
atgcaccagt ttcctttg                                                  138

<210> SEQ ID NO 11
<211> LENGTH: 104
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
atgaagaaaa ccaggtttgg agcgtttttc tttacgatga tgtcaagaag gttgttggcg    60
ataaggagct gttttcctcc tgcatgccac agcagaagct tggg                     104

<210> SEQ ID NO 12
<211> LENGTH: 94
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
aatggatggt atgcatcctg cttgttcttg ccgttgagca gtgcgcgtgg cagtgcctgg    60
cggcggttca gaacgttcat attagtcgac gcgt                                94

<210> SEQ ID NO 13
<211> LENGTH: 148
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
cccaagcttc tgctgtggca tgcaggagga aaacagctcc ttatcgccaa caaccttctt    60
gacatcatcg taaagaaaaa cgctccaaac ctggttttct tcatcaaagg aaactggtgc    120
```

-continued atccttgcgc atggattcgt accatgga            148

<210> SEQ ID NO 14
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
acatgcatgc cacagcagac cagctctatt ggaaactcca tcattagcat ggacccacca     60
aagcatacca agatccgttc cgtcgttaac aaggcattta ctccgcgcgc tatgaagcag    120

<210> SEQ ID NO 15
<211> LENGTH: 120
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tgggaaccac gcattcagga aatcaccgat gaactgattc agaagtttca gggccgcagt     60
gagtttgacc ttgttcacga ttattcctac ccacttccag ttattgttat ctctgagctg    120

<210> SEQ ID NO 16
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ctgggagttc cttccgcaca tatggaacag tttaaggcat ggtcagatct taagcttggg     60

<210> SEQ ID NO 17
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tggtgggtcc atgctaatga tggagtttcc aatagagctg gtctgctgtg gcatgcatgt     60

<210> SEQ ID NO 18
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
actgcggccc tgaaacttct gaatcagttc atcggtgatt tcctgaatgc gtggttccca     60
ctgcttcata gcgcgcggag taaatgcctt gttaacgacg aacggatct tggtatgctt    120

<210> SEQ ID NO 19
<211> LENGTH: 120
<212> TYPE: DNA
<213> ORGANISM: Artificial Sequence
<220> FEATURE:

```
<223> OTHER INFORMATION: Description of Artificial Sequence: Synthetic
      polynucleotide

<400> SEQUENCE: 19
cccaagctta agatctgacc atgccttaaa ctgttccata tgtgcggaag gaactcccag      60
cagctcagag ataacaataa ctggaagtgg gtaggaataa tcgtgaacaa ggtcaaactc     120

<210> SEQ ID NO 20
<211> LENGTH: 130
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
acgcgtcgac taatgatatc cgccgccatc caaacccaca tattgcattt ggccacggca      60
tccatttttg ccttggcgca ccacttgcac gtcttgaagc aaacattgca ctgacctctc     120
tgatttctgc                                                            130

<210> SEQ ID NO 21
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ttttcctcat atggagtgcg tctccatcac tccaatcgaa aactccgtta tctacggact      60
gaagagcttc cgtgttaaga tgtaaggatc cggg                                  94

<210> SEQ ID NO 22
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
agacgtgcaa gtggtgcgcc aaggcaaaaa tggatgccgt ggccaaatgc aatatgtggg      60
tttggatggc ggcggatatc attagtcgac gcgt                                  94

<210> SEQ ID NO 23
<211> LENGTH: 130
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
cccggatcct tacatcttaa cacggaagct cttcagtccg tagataacgg agttttcgat      60
tggagtgatg gagacgcact ccatatgagg aaaagcagaa atcagagagg tcagtgcaat     120
gtttgcttca                                                            130

<210> SEQ ID NO 24
<211> LENGTH: 120
<212> TYPE: DNA
<213> ORGANISM: Artificial Sequence
<220> FEATURE:
<223> OTHER INFORMATION: Description of Artificial Sequence: Synthetic
``` polynucleotide

<400> SEQUENCE: 24
acgcgtcgac atgccctcag gcagttgagg aagccctgcg tttccgcgca ccagcaccag     60
ttctgcgccg catcgcaaag cgcgataccg agatcggcgg ccacctgatt aaggaaggtg    120

<210> SEQ ID NO 25
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
atacggttct ggcatttgtt gcatccgcaa accgtgatga agcaaagttt gaccgcccac     60
acatgtttga tatccgc                                                    77

<210> SEQ ID NO 26
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
tgcgatgcgg cgcagaactg gtgctggtgc gcggaaacgc agggcttcct caactgcctg     60
agggcatgtc gacgcgt                                                    77

<210> SEQ ID NO 27
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
gcggatatca aacatgtgtg gcggtcaaa ctttgcttca tcacggtttg cggatgcaac      60
aaatgccaga accgtatcac cttccttaat caggtggccg ccgatctcgg tatcgcgctt   120

<210> SEQ ID NO 28
<211> LENGTH: 130
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
acgcgtcgac cagatcttct ggtctccacc ccaaaggata agtccgaaga agctgaaaag     60
gcatttctgg aagaacgcga taagtgcgag gaagaactgg cagcattttt tgcaggcatc   120
atcgaagaaa                                                           130

<210> SEQ ID NO 29
<211> LENGTH: 130
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
agcgcaacaa gccggaacag gatattattt ctattctggt tgaagcagaa gaaaccggcg    60
agaagctgtc cggtgaagag ctgattccgt tgtgcaccct gctgctggtt gcaggaaacg   120
aaaccactac                                                         130

<210> SEQ ID NO 30
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
caacctgatt tccaacgcaa tgttcagcat cctggaaacc ccaggcgttt acgaggaact    60
gcgcagccat cctgaactga tgcctcaggc agt                                93

<210> SEQ ID NO 31
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ttcctcgcac ttatcgcgtt cttccagaaa tgcctttca gcttcttcgg acttatcctt    60
tggggtggag accagaagat ctggtcgacg cgt                                93

<210> SEQ ID NO 32
<211> LENGTH: 130
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
acaacggaat cagctcttca ccggacagct tctcgccggt ttcttctgct tcaaccagaa    60
tagaaataat atcctgttcc ggcttgttgc gcttttcttc gatgatgcct gcaaaaaatg   120
ctgccagttc                                                         130

<210> SEQ ID NO 33
<211> LENGTH: 130
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
actgcctgag gcatcagttc aggatggctg cgcagttcct cgtaaacgcc tggggtttcc    60
aggatgctga acattgcgtt ggaaatcagg ttggtagtgg tttcgtttcc tgcaaccagc   120
agcagggtgc                                                         130

<210> SEQ ID NO 34
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
acgccgcgac gcgtcgacta atatgaacgt tctgaacc　　　　　　　　　　　　　38

<210> SEQ ID NO 35
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gcgacgcgcg ggatccttac atcttaacac ggaagctc　　　　　　　　　　　　　38

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
cgccagggtt ttcccagtca cgac　　　　　　　　　　　　　　　　　　　　24

<210> SEQ ID NO 37
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
tagtggatcc atagtcgact aatcccdta　　　　　　　　　　　　　　　　　29

<210> SEQ ID NO 38
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
agcggtcgac aatgaatgtg ttaaaccgc　　　　　　　　　　　　　　　　　29

<210> SEQ ID NO 39
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
acgcggatcc ttacattttc acacggaag　　　　　　　　　　　　　　　　　29

<210> SEQ ID NO 40
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40

```
tcgcctcgag tcgaggaggt cgactaatat gaacgttctg aaccgccgtc aagccttgca    60
gcgagcg                                                              67
```

<210> SEQ ID NO 41
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41

```
acgccgcgac gcgtcgacta atatgaacgt tctgaacc                            38
```

<210> SEQ ID NO 42
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42

```
gcgacgcgcg ggatccttac atcttaacac ggaagctc                            38
```

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43

```
cagctggaag agcaactgg                                                 19
```

<210> SEQ ID NO 44
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44

```
ggtatgcttt ggtgggtcca tgttaatgat ggag                                34
```

<210> SEQ ID NO 45
<211> LENGTH: 396
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

```
Met Asn Val Leu Asn Arg Arg Gln Ala Leu Gln Arg Ala Leu Leu Asn
 1               5                  10                  15

Gly Lys Asn Lys Gln Asp Ala Tyr His Pro Phe Pro Trp Tyr Glu Ser
                20                  25                  30

Met Arg Lys Asp Ala Pro Val Ser Phe Asp Glu Glu Asn Gln Val Trp
            35                  40                  45

Ser Val Phe Leu Tyr Asp Asp Val Lys Val Val Gly Asp Lys Glu
        50                  55                  60

Leu Phe Ser Ser Cys Met Pro Gln Gln Thr Ser Ser Ile Gly Asn Ser
```

```
                65                  70                  75                  80
Ile Ile Asn Met Asp Pro Pro Lys His Thr Lys Ile Arg Ser Val Val
                    85                  90                  95

Asn Lys Ala Phe Thr Pro Arg Ala Met Lys Gln Trp Glu Pro Arg Ile
                100                 105                 110

Gln Glu Ile Thr Asp Glu Leu Ile Gln Lys Phe Gln Gly Arg Ser Glu
                115                 120                 125

Phe Asp Leu Val His Asp Phe Ser Tyr Pro Leu Pro Val Ile Val Ile
            130                 135                 140

Ser Glu Leu Leu Gly Val Pro Ser Ala His Met Glu Gln Phe Lys Ala
145                 150                 155                 160

Trp Ser Asp Leu Leu Val Ser Thr Pro Lys Asp Lys Ser Glu Glu Ala
                165                 170                 175

Glu Lys Ala Phe Leu Glu Glu Arg Asp Lys Cys Glu Glu Leu Ala
                180                 185                 190

Ala Phe Phe Ala Gly Ile Ile Glu Glu Lys Arg Asn Lys Pro Glu Gln
            195                 200                 205

Asp Ile Ile Ser Ile Leu Val Glu Ala Glu Thr Gly Glu Lys Leu
    210                 215                 220

Ser Gly Glu Glu Leu Ile Pro Leu Cys Thr Leu Leu Val Ala Gly
225                 230                 235                 240

Asn Glu Thr Thr Thr Asn Leu Ile Ser Asn Ala Met Tyr Ser Ile Leu
                245                 250                 255

Glu Thr Pro Gly Val Tyr Glu Glu Leu Arg Ser His Pro Glu Leu Met
                260                 265                 270

Pro Gln Ala Val Glu Glu Ala Leu Arg Phe Arg Ala Pro Ala Pro Val
            275                 280                 285

Leu Arg Arg Ile Ala Lys Arg Asp Thr Glu Ile Gly Gly His Leu Ile
    290                 295                 300

Lys Glu Gly Asp Met Val Leu Ala Phe Val Ala Ser Ala Asn Arg Asp
305                 310                 315                 320

Glu Ala Lys Phe Asp Arg Pro His Met Phe Asp Ile Arg Arg His Pro
                325                 330                 335

Asn Pro His Ile Ala Phe Gly His Gly Ile His Phe Cys Leu Gly Ala
                340                 345                 350

Pro Leu Ala Arg Leu Glu Ala Asn Ile Ala Leu Thr Ser Leu Ile Ser
            355                 360                 365

Ala Phe Pro His Met Glu Cys Val Ser Ile Thr Pro Ile Glu Asn Ser
    370                 375                 380

Val Ile Tyr Gly Leu Lys Ser Phe Arg Val Lys Met
385                 390                 395

<210> SEQ ID NO 46
<211> LENGTH: 396
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Met Asn Val Leu Asn Arg Arg Gln Ala Leu Pro Arg Ala Leu Leu Asn
1               5                   10                  15

Gly Lys Asn Lys Gln Asp Ala Tyr His Pro Phe Pro Trp Tyr Glu Ser
                20                  25                  30

Met Arg Lys Asp Ala Pro Val Ser Phe Asp Glu Glu Asn Gln Val Trp
```

```
                35                  40                  45
Ser Val Phe Leu Tyr Asp Asp Val Lys Lys Val Gly Asp Lys Glu
             50                  55                  60

Leu Phe Ser Ser Cys Met Pro Gln Gln Thr Ser Ser Ile Gly Asn Ser
 65                  70                  75                  80

Ile Ile Ser Met Asp Pro Pro Lys His Thr Lys Ile Arg Ser Val Val
                 85                  90                  95

Asn Lys Ala Phe Thr Pro Arg Ala Met Lys Gln Trp Glu Pro Arg Ile
                100                 105                 110

Gln Glu Ile Thr Asp Glu Leu Ile Gln Lys Phe Gln Gly Arg Ser Glu
                115                 120                 125

Phe Asp Leu Val His Asp Tyr Ser Tyr Pro Leu Pro Val Ile Val Ile
                130                 135                 140

Ser Glu Leu Leu Gly Val Pro Ser Ala His Met Glu Gln Phe Lys Ala
145                 150                 155                 160

Trp Ser Asp Leu Leu Val Ser Thr Pro Lys Asp Lys Ser Glu Glu Ala
                165                 170                 175

Glu Lys Ala Phe Leu Glu Glu Arg Asp Lys Cys Glu Glu Glu Leu Ala
                180                 185                 190

Ala Phe Phe Ala Gly Ile Ile Glu Glu Lys Arg Asn Lys Pro Glu Gln
                195                 200                 205

Asp Ile Ile Ser Ile Leu Val Glu Ala Glu Thr Gly Glu Lys Leu
                210                 215                 220

Ser Gly Glu Glu Leu Ile Pro Leu Cys Thr Leu Leu Leu Val Ala Gly
225                 230                 235                 240

Asn Glu Thr Thr Thr Asn Leu Ile Ser Asn Ala Met Phe Ser Ile Leu
                245                 250                 255

Glu Thr Pro Gly Val Tyr Glu Glu Leu Arg Ser His Pro Glu Leu Met
                260                 265                 270

Pro Gln Ala Val Glu Glu Ala Leu Arg Phe Arg Ala Pro Ala Pro Val
                275                 280                 285

Leu Arg Arg Ile Ala Lys Arg Asp Thr Glu Ile Gly Gly His Leu Ile
                290                 295                 300

Lys Glu Gly Asp Thr Val Leu Ala Phe Val Ala Ser Ala Asn Arg Asp
305                 310                 315                 320

Glu Ala Lys Phe Asp Arg Pro His Met Phe Asp Ile Arg Arg His Pro
                325                 330                 335

Asn Pro His Ile Ala Phe Gly His Gly Ile His Phe Cys Leu Gly Ala
                340                 345                 350

Pro Leu Ala Arg Leu Glu Ala Asn Ile Ala Leu Thr Ser Leu Ile Ser
                355                 360                 365

Ala Phe Pro His Met Glu Cys Val Ser Ile Thr Pro Ile Glu Asn Ser
                370                 375                 380

Val Ile Tyr Gly Leu Lys Ser Phe Arg Val Lys Met
385                 390                 395
```